US010806330B2

(12) United States Patent
Morishima et al.

(10) Patent No.: US 10,806,330 B2
(45) Date of Patent: Oct. 20, 2020

(54) SINGLE USE ENDOSCOPE DEVICE

(71) Applicant: HOYA CORPORATION, Tokyo (JP)

(72) Inventors: Takayoshi Morishima, Tokyo (JP); Kohei Iketani, Saitama (JP); Keiji Ito, Saitama (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 16/499,805

(22) PCT Filed: May 31, 2018

(86) PCT No.: PCT/JP2018/021015
§ 371 (c)(1),
(2) Date: Sep. 30, 2019

(87) PCT Pub. No.: WO2018/221672
PCT Pub. Date: Dec. 6, 2018

(65) Prior Publication Data
US 2020/0100655 A1    Apr. 2, 2020

Related U.S. Application Data

(63) Continuation-in-part of application No. PCT/JP2017/024394, filed on Jul. 3, 2017.
(Continued)

(51) Int. Cl.
*A61B 1/00* (2006.01)
*A61B 1/005* (2006.01)
(Continued)

(52) U.S. Cl.
CPC ........ *A61B 1/0051* (2013.01); *A61B 1/00009* (2013.01); *A61B 1/00071* (2013.01);
(Continued)

(58) Field of Classification Search
None
See application file for complete search history.

(56) References Cited

U.S. PATENT DOCUMENTS

| 5,193,525 A * | 3/1993 | Silverstein ......... | A61B 1/00096 600/123 |
| 2005/0085694 A1* | 4/2005 | Nakao ................ | A61B 1/00073 600/153 |

(Continued)

FOREIGN PATENT DOCUMENTS

| EP | 2151183 A1 | 2/2010 |
| EP | 2596738 A1 | 5/2013 |

(Continued)

OTHER PUBLICATIONS

English translation of International Search Report dated Aug. 1, 2017, in international application No. PCT/JP2017/024394.
(Continued)

*Primary Examiner* — Timothy J Neal
(74) *Attorney, Agent, or Firm* — Kilpatrick Townsend & Stockton LLP

(57) ABSTRACT

A single use endoscope device which is inserted inside a subject includes: a distal end portion which includes at least an imaging element; an operation unit which operates an operation of the endoscope device; a curved portion which can be curved inside the subject by operating the operation unit; a fractured portion which detaches the distal end portion from the curved portion; and a soft portion which is extended from the operation unit to the curved portion. The distal end portion, the curved portion and the soft portion are inserted in the subject, the operation unit, the curved portion, and the soft portion are discarded after use of the endoscope device, and the distal end portion and at least the imaging element included in the distal end portion are reused.

20 Claims, 23 Drawing Sheets

Related U.S. Application Data

(60) Provisional application No. 62/513,903, filed on Jun. 1, 2017.

(51) Int. Cl.
   *A61B 1/05* (2006.01)
   *A61B 1/06* (2006.01)

(52) U.S. Cl.
   CPC ...... *A61B 1/00091* (2013.01); *A61B 1/00096* (2013.01); *A61B 1/00098* (2013.01); *A61B 1/053* (2013.01); *A61B 1/051* (2013.01); *A61B 1/0684* (2013.01)

(56) References Cited

U.S. PATENT DOCUMENTS

| | | | |
|---|---|---|---|
| 2005/0272975 A1 | 12/2005 | McWeeney et al. | |
| 2007/0118019 A1 | 5/2007 | Mitani et al. | |
| 2011/0037876 A1* | 2/2011 | Talbert | A61B 1/00055 348/231.99 |
| 2013/0131452 A1* | 5/2013 | Kuroda | A61B 1/0008 600/136 |
| 2013/0172670 A1 | 7/2013 | Levy et al. | |

FOREIGN PATENT DOCUMENTS

| | | |
|---|---|---|
| JP | 2-246920 A | 10/1990 |
| JP | 4-261635 A | 9/1992 |
| JP | 6-254047 A | 9/1994 |
| JP | 7-327923 A | 12/1995 |
| JP | 8-24208 A | 1/1996 |
| JP | 8-112245 A | 5/1996 |
| JP | 2002-236260 A | 8/2002 |
| JP | 2004-229947 A | 8/2004 |
| JP | 2006-15076 A | 1/2006 |
| JP | 2006-75238 A | 3/2006 |
| JP | 2006-116128 A | 5/2006 |
| JP | 2006-149689 A | 6/2006 |
| JP | 2006-149844 A | 6/2006 |
| JP | 2006-296675 A | 11/2006 |
| JP | 2006325691 A | 12/2006 |
| JP | 2006340878 A | 12/2006 |
| JP | 2007-530155 A | 11/2007 |
| JP | 2009-148420 A | 7/2009 |
| JP | 4676427 B2 | 4/2011 |
| JP | 2013-123647 A | 6/2013 |
| WO | 2004/086957 A2 | 10/2004 |
| WO | 2005094665 A2 | 10/2005 |
| WO | 2014111943 A2 | 7/2014 |
| WO | 2016/199478 A1 | 12/2016 |

OTHER PUBLICATIONS

English translation of International Search Report dated Aug. 22, 2017, in international application No. PCT/JP2017/024395.

English translation of International Search Report dated Aug. 21, 2018, in international application No. PCT/JP2018/021015.

EP17911415.2, Supplementary Partial European Search Report, dated Feb. 25, 2020, 9 pages.

* cited by examiner

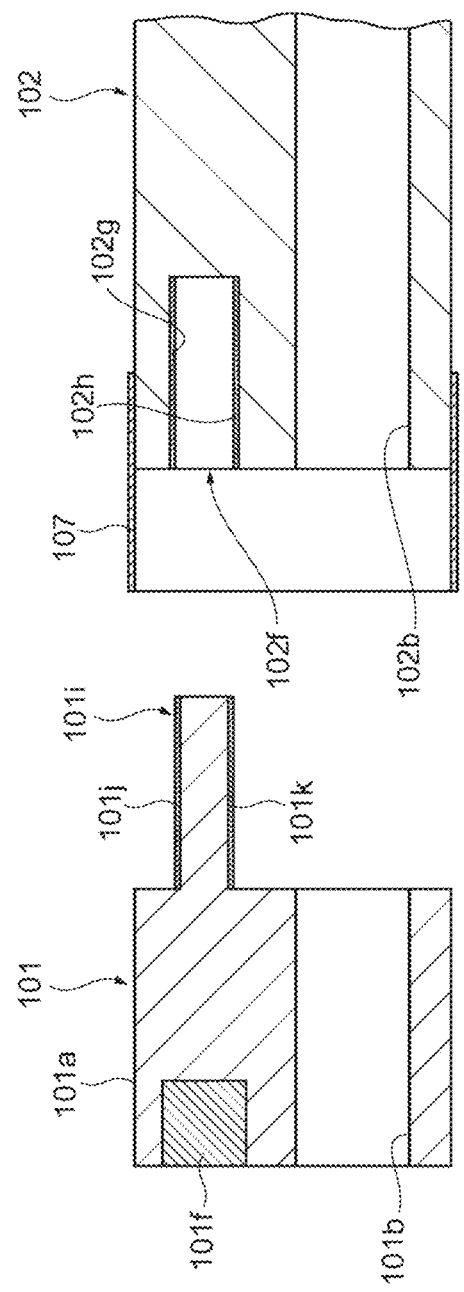

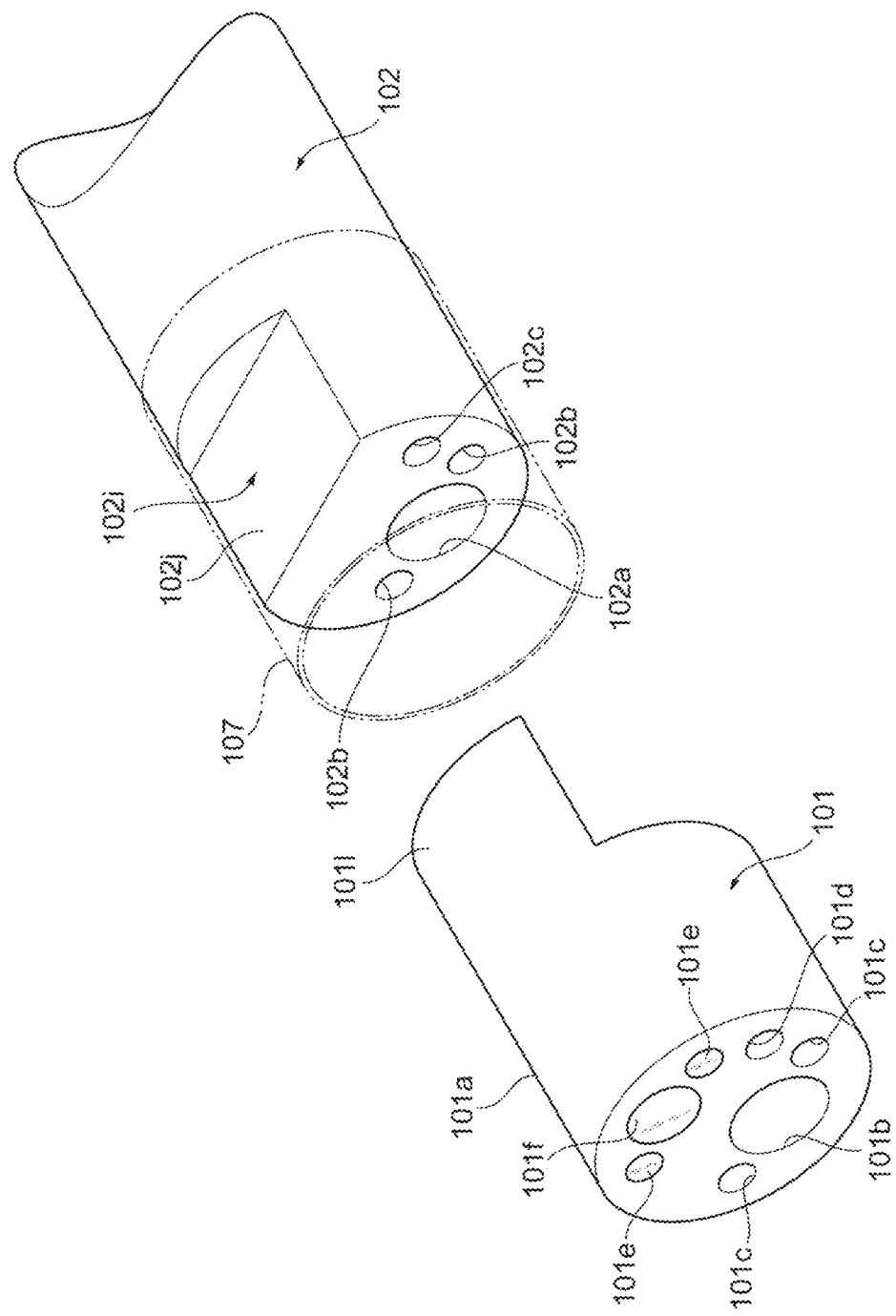

SINGLE USE ENDOSCOPE DEVICE

This application is the national phase application under 35 U.S.C. § 371 of international application No. PCT/JP2018/021015, filed on May 31, 2018, which claims priority to U.S. provisional application No. 62/513,903 filed in the U.S.A. on Jun. 1, 2017, and International Application No. PCT/JP2017/024394 filed on Jul. 3, 2017, the entire contents of which are incorporated by reference herein.

TECHNICAL FIELD

The present disclosure relates to a single use endoscope device.

BACKGROUND ART

There has been a concept of a single use endoscope from before. For example, Patent Literature 1 discloses making single use of all endoscopes connected with an endoscope system. Consequently, it is possible to solve a disadvantage caused by cleaning and reusing the endoscopes. For example, it is possible to eliminate an infection risk in a case where cleaning or disinfection is imperfect after use of the endoscopes, and omit a cleaning labor on a hospital side.

CITATION LIST

Patent Literature

Patent Literature 1: JP 4676427 B2

SUMMARY OF INVENTION

Technical Problem

However, the endoscope disclosed in Patent Literature 1 discards an imaging unit, too, which is housed at a distal end of the endoscope. Therefore, in order to suppress cost of the endoscope itself, performance (e.g., the number of pixels (image quality)) of the imaging unit cannot help being sacrificed. On the other hand, using an imaging element and a lens having performance equal to that of a general reuse endoscope to secure image quality of the imaging unit increases cost of the endoscope. This high cost is finally passed to patients, and is one of the biggest factors that a single use endoscope is not popular. In this case, while it is possible to carry out endoscope inspection while maintaining a high cleaning level at all times, it is not possible to enjoy a maximum advantage of a single use endoscope which can omit a labor for cleaning the endoscope device.

The present disclosure has been made in light of such a situation, and realizes a single use endoscope which solves both of a problem in terms of cost and a problem in terms of image quality.

Solution to Problem

To solve the above problems, the present embodiment provides a single use endoscope device which is inserted inside a subject, and which includes: a distal end portion which includes at least an imaging element; an operation unit which operates the endoscope device; a curved portion which can be curved inside the subject by operating the operation unit; a fractured portion which detaches the distal end portion from the curved portion; and a soft portion which is extended from the operation unit to the curved portion, wherein the distal end portion or at least the imaging element included in the distal end portion is reused, and a portion located closer to a side of the operation unit than a reuse portion is formed as a single use portion.

Further features related to the present disclosure will be made more apparent from disclosure and the accompanying drawings of this description. Furthermore, an aspect of the present disclosure is achieved and realized by combinations of elements and various elements, subsequent detailed description, and the aspect of the accompanying claims.

It should be understood that the disclosure of this description is only typically exemplary, and by no means limits the claims or application examples of the present disclosure in any respect.

Advantageous Effects of Invention

A single use endoscope according to the present disclosure can solve both of the problem in terms of cost and the problem in terms of cost compatible.

BRIEF DESCRIPTION OF DRAWINGS

FIG. 5A is a cross-sectional view illustrating the relationship between the distal end portion 101 and the curved portion 102 of the endoscope according to modified example 1.

FIG. 6B is a perspective view illustrating the relationship between the distal end portion 101 and the curved portion 102 of the endoscope according to modified example 2.

FIG. 14A is a cross-sectional view in a longitudinal direction of the insertion portion. FIG. 14B is a view illustrating a distal end of the insertion portion from a front surface.

DESCRIPTION OF EMBODIMENTS

Hereinafter, an embodiment of the present disclosure will be described with reference to the accompanying drawings. The accompanying drawings illustrate the functionally same components with the same numbers in some cases. In this regard, the accompanying drawings illustrate the specific embodiment and implementation examples which conform to the principal of the present disclosure. However, these embodiment and implementation examples help understand the present disclosure, and are by no means used to interpret the present disclosure in a limited manner.

The present embodiment will be sufficiently described for one of ordinary skilled in the art to carry out the present disclosure. However, it is necessary to understand that the other implementations and aspects are possible, and configurations and structures can be variously changed and multiple components can be replaced without departing from the scope and the spirit of the technical idea of the present disclosure. Therefore, the following description should not be limited to this and interpreted. In addition, in the following description, an "axial direction" indicates an axial direction of an insertion portion of an endoscope, a "front side" indicates a subject side, and a "rear side" indicates an operation unit side of the endoscope.

Configuration of Endoscope System

Figure 1:
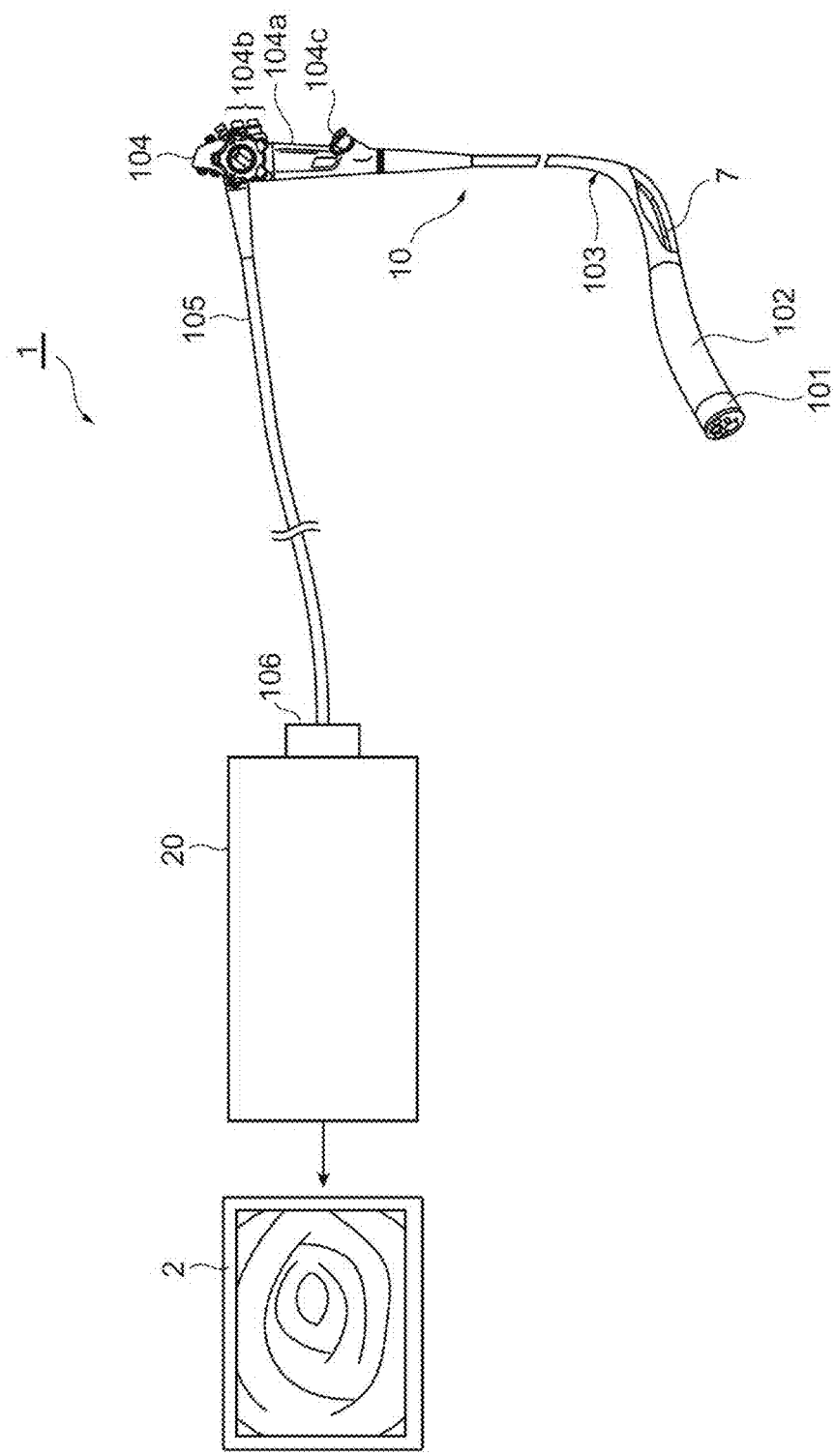
FIG. 1 is a schematic configuration diagram illustrating an endoscope system according to an embodiment.

FIG. 1 is a schematic configuration diagram illustrating an endoscope system according to the embodiment. FIG. 1 illustrates connection between devices as an arrow for ease of illustration of the drawings, and breaks and illustrates part of components.

An endoscope system 1 according to the present embodiment includes an endoscope 10, a video processor 20 which is connected with a connector portion 106 of the endoscope 10, and a monitor 2 which is connected with the video processor 20 and displays an image imaged by the endoscope 10.

The endoscope 10 includes a distal end portion 101 which is inserted inside a subject (not illustrated) and includes an imaging unit, a curved portion 102 which can be curved in a body of the subject, a soft portion 103 of a thin and long tube shape, an operation unit 104 which is connected with the soft portion 103 and accepts an operation of a user (operator), a connector cable portion 105 which extends from the operation unit 104 and is connected with the video processor 20, and a connector portion 106 which is a portion to be connected with the video processor 20. Furthermore, the curved portion 102 to the connector portion 106 of the endoscope 10 according to the present embodiment are single-use. However, only the distal end portion 101 or only an imaging unit 21 included in the distal end portion 101 (e.g., a structure in which a member (e.g., resin member) which houses the imaging element is removed and the imaging element is exposed in the distal end portion 101) can be detached from the endoscope 10, and cleaned and reused (see FIGS. 2, 4, 5B, and 6B). In addition, the distal end portion 101, the curved portion 102, and the soft portion 103 can be also collectively referred to as an insertion portion. In this regard, a boundary between a portion to be reused, and a single use portion is a boundary between the distal end portion 101 and the curved portion 102, yet can be a predetermined intermediate position of the curved portion 102 or a predetermined intermediate position of the soft portion 103.

Portions of the endoscope 10 to be inserted inside the body of the subject are the curved portion 102 which are coaxially coupled to the distal end portion 101 and the soft portion 103, is formed relatively short and is free to be curved, and the soft portion (insertion flexible tube) 103 which is coupled to the operation unit 104 and is formed relatively long.

Inside the soft portion 103 and the curved portion 102, an imaging signal cable and a power supply cable extend along an axial direction of the soft portion 103 and the curved portion 102. Furthermore, although not illustrated, the soft portion 103 and the curved portion 102 include a built-in treatment tool insertion channel, two air supply/water supply tubes, a sub water supply tube, and a guide tube which allows insertion of an angle wire and has a spiral shape or a tube shape (or may employ a configuration including a closely wound coil made of a guide metal). In addition, the soft portion 103 and the curved portion 102 may include a built-in an illumination light guide fiber bundle.

As illustrated in FIG. 1, the operation unit 104 includes an operation unit main body 104a which forms an operation grip portion, and a treatment tool insertion port 104c which is provided on a side of the operation unit main body 104a close to the soft portion 103. The treatment tool insertion port 104c is an opening of the above treatment tool insertion channel on a side of the operation unit 104. Furthermore, the operation unit main body 104a is provided with a curving operation knob for performing an operation of curving the curved portion 102, and switches which are related to each operation of the endoscope 10.

The video processor 20 is a device which processes image data imaged by an imaging unit (imaging element) 21 included in the distal end portion 101 of the endoscope 10 and transmitted via the imaging signal cable, and generates a video signal. This video processor 20 further outputs the generated video signal to the monitor 2. Thus, an internal image of the subject is displayed on the monitor 2.

Entire Configuration of Endoscope

Figure 2:
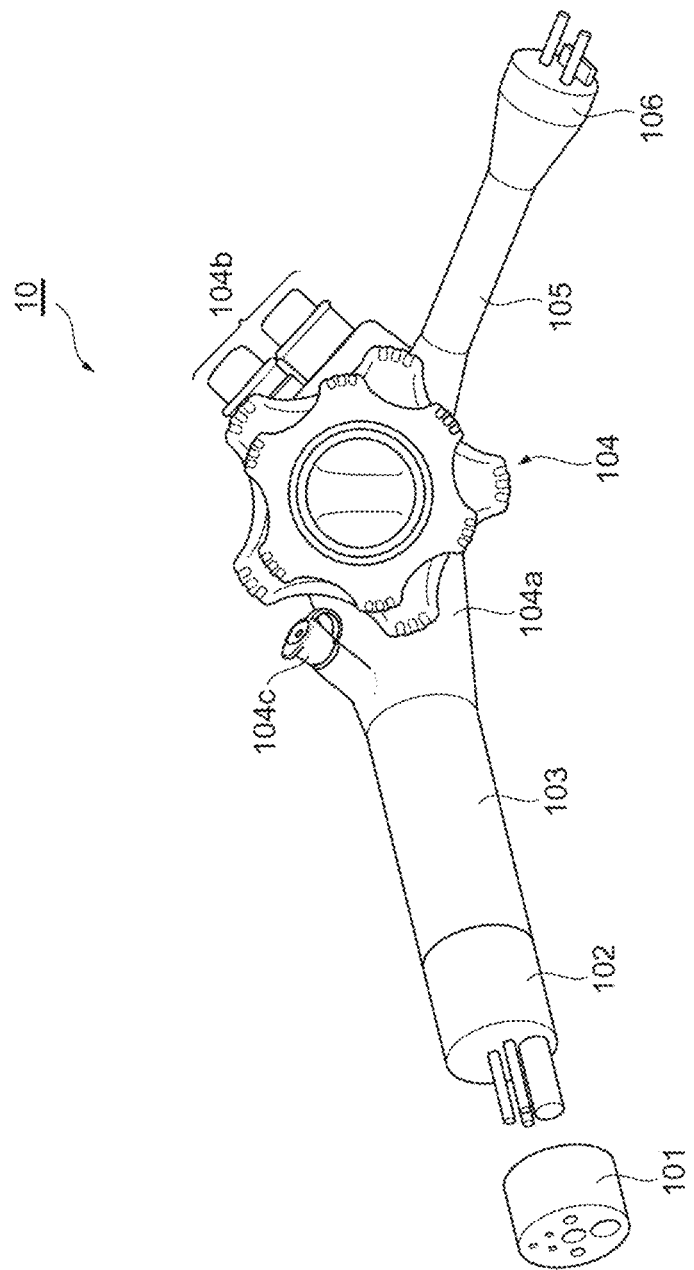
FIG. 2 is a view illustrating an entire configuration of a single use endoscope 10.

Although the single use endoscope 10 has been described with reference to FIG. 1, the single use endoscope 10 will be described in more detail hereinafter. FIG. 2 is a view illustrating an entire configuration of the single use endoscope 10. In addition, in FIG. 2, the position and the shape of the operation unit 104 of the endoscope 10 are different from an actual position and shape for convenience of illustration.

The single use endoscope 10 includes, for example, the distal end portion 101, the curved portion 102, the soft portion 103, the operation unit 104, the connector cable portion 105, and the connector portion 106. The curved portion 102, the soft portion 103, the operation unit 104, the connector cable portion 105, and the connector portion 106 other than the distal end portion 101 can be formed by a resin having higher flexibility (softer) than that of the distal end portion 101. In addition, the resin used for the curved portion 102, the soft portion 103, and the connector cable portion 105 is preferably a multi-lumen structure. Such a highly flexible resin is, for example, polytetrafluoroethylene (PTFE), expanded PTFE (ePTFE), polyethylene (PE), high density polyethylene (HDPE), and polypropylene (PP) (the above are porous materials), and polyurethane (PU), polypropylene (PP), polyethylene (PE), and polyamide (the above are non-porous materials). In the single use endoscope 10, most of metal parts and members which are other than members such the imaging element included in the distal end portion 101 to be reused, and which are used in conventional endoscopes may be substituted with resin members.

The distal end portion 101 includes, for example, the imaging element such as a CMOS or a CCD, a small LED which is a light, a memory (which may be a memory built in the imaging element or may be an RFID tag mounted separately from the imaging element), an objective lens which is attached to the imaging element, a light distribution lens which is attached to the LED, a forceps port, an air supply port (which is used in place of an air supply nozzle of the conventional endoscope), a water supply port (which is used in place of a water supply nozzle of the conventional endoscope), and a water jet port. The distal end portion 101 may be configured to cover the imaging element, the small LED, and the memory with a resin which has greater hardness than the other portions of the endoscope 10 and does not deform. In this case, the portions which correspond to the nozzles (the air supply nozzle and the water supply nozzle) and the illumination lens are preferably molded integrally with the distal end portion 101 by a resin. A super-wide-angle lens can be used for the objective lens, and a resin thin film of a flat plate shape may be attached to the objective lens to prevent contamination. The distal end portion 101 and the curved portion 102 are connected by adhesion means such as a tape or an adhesive, and adopt such a structure that a user (e.g., hospital) cannot detach the distal end portion 101 from the endoscope 10. Furthermore, even if the distal end portion 101 is detached from the endoscope 10, the detachment deforms or damages part of the distal end portion 101 (e.g., an internal structure or a structure of an attachment portion with respect to the endoscope 10), and the user may not be allowed to reuse the distal end portion 101. In addition, the imaging element and the small LED housed in the distal end portion 101 may have performance equal to those accommodated at the distal end portion of a general reuse-type endoscope. Hence, these imaging element and small LED are expensive. Therefore, after the single use endoscope 10 is collected from the hospital, the distal end portion 101 or the imaging element housed inside the distal end portion 101 is cleaned by a manufacturer of the endoscope 10 or a vendor or reused. The curved portion 102, the soft portion 103, the operation unit 104, and the connector cable portion 105 other than the distal end portion 101 are discarded (e.g., incinerated). That is, the cleaned and sterilized distal end portion 101, and the completely new curved portion 102, soft portion 103, operation unit 104, and connector cable portion 105 are used to produce the new single use endoscope 10 to provide to the hospital side again.

The curved portion 102 is entirely made of the resin as described above. For example, the resin of the multi-lumen structure is preferably used for the curved portion 102. Furthermore, as illustrated in FIG. 2, a resin tube which forms the forceps pipe, a resin tube which forms the air supply tube, the resin tube which forms the water supply tube and a resin tube which forms the sub water supply tube in the curved portion 102 protrude from an end surface of the curved portion 102. When illumination light is introduced by an optical fiber instead of an LED, the illumination light guide fiber bundle also protrudes from the end surface. In addition, each of the four resin tubes is inserted in each insertion port (the forceps port, the air supply port, the water supply port, and the water jet port) of the distal end portion 101 connected with the curved portion 102, so that the distal end portion 101 and the curved portion 102 are coupled fast.

The soft portion 103 can be formed by, for example, a spiral tube made of the resin or can be formed by using the resin of the multi-lumen structure. In the soft portion 103, a metal blade or a wire is not inserted and, instead, a resin tube having greater hardness than the resin used for an outer portion (surface portion) of the soft portion 103 is inserted. Consequently, it is possible to adopt a structure that only the curved portion 102 can be curved. Furthermore, built-in components of the soft portion 103 and the curved portion 102 are the above resin wire (a resin angle wire) or the metal wire and a resin tube having high hardness, and, in addition, power supply/signal transmission/switch electrical cables. In addition, when a signal is wirelessly transmitted, the built-components are, for example, a resin angle wire or a metal angle wire, a resin stay coil, a power supply electrical wire (electrical cable), an electrical signal transmission electrical wire from a signal antenna installed in the soft portion, and a switch cable.

Preferably, the operation unit 104 is also entirely made of a resin. The operation unit 104 includes, for example, the operation unit main body 104a which forms the operation grip portion, the electrical switch 104b, and the treatment tool insertion port 104c which is provided on a side of the operation unit main body 104a close to the soft portion 103. The user (e.g., an operator such as a doctor) performs an operation of suctioning, air supply and water supply by, for example, using the electrical switch 104b provided to the operation unit 104. It is possible to switch various operations by using the electrical switch 104b in this way, so that it is possible to completely prevent a blowout due to a reverse flow of a mucus and a blood. Furthermore, an internal structure of the operation unit 104 can be integrally molded by using die slide injection.

Preferably, the connector cable portion 105 and the connector portion 106 are also entirely made of the resin. The connector cable portion 105 houses part of the cables which extend from the video processor 20 to the distal end portion 101. The connector portion 106 includes an electrical circuit or an electronic circuit. These components are provided on a side of the video processor 20. Furthermore, the connector portion 106 includes, for example, an insertion-type electrical socket, a memory (example: RFID tag) which stores a serial number for managing the endoscope 10, a suction nipple (made of a resin), an air supply nipple (made of the resin), a water supply nipple (made of the resin), and a water jet port.

<Front Surface Configuration of Distal End Portion of Endoscope>

Figure 3:
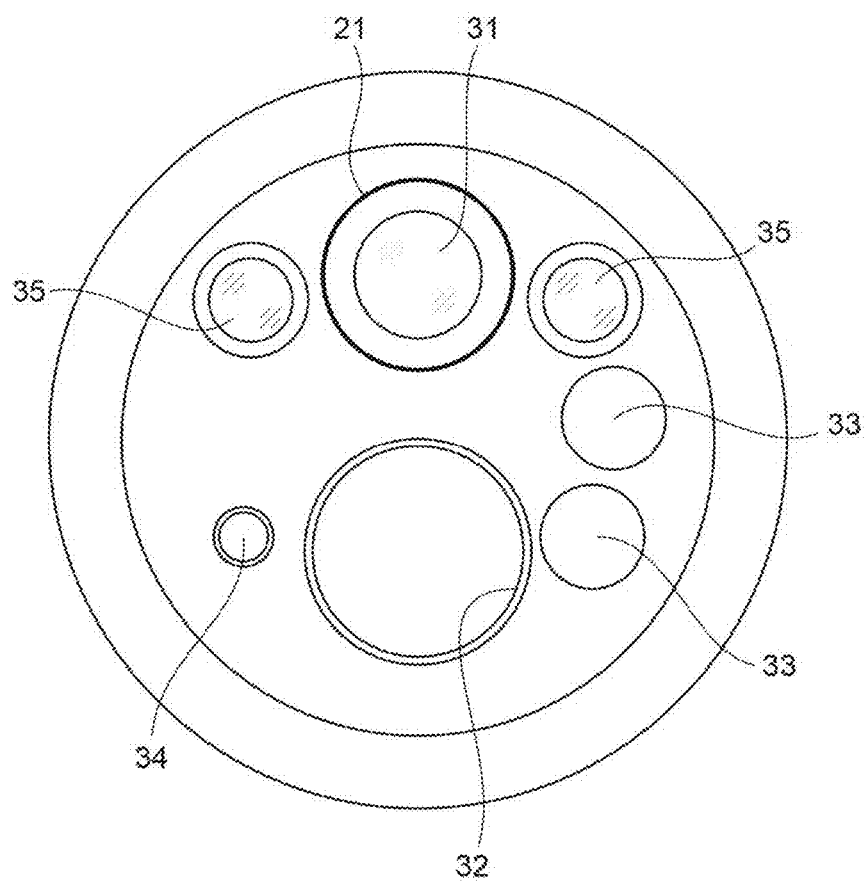
FIG. 3 is a view illustrating a front configuration illustrating a distal end portion 101 of the endoscope 10.

FIG. 3 is a view illustrating a front configuration illustrating the distal end portion 101 of the endoscope 10. In the distal end portion 101, for example, an objective lens 31 of the imaging unit (including the imaging element such as the CMOS or the CCD) 21, a forceps port 32 which functions as a treatment tool insertion channel, an air supply port/water supply port 33 to which the two air supply/water supply tubes are attached, respectively, a water jet port 34 to which the sub water supply tube is attached, and a light distribution lens 35 which is installed for the illumination light (LED) are respectively disposed. Although the LED is used as the illumination light, a light guide fiber bundle formed by bundling optical fibers may be used.

Relationship Between Distal End Portion and Curved Portion of Endoscope

Figure 4:
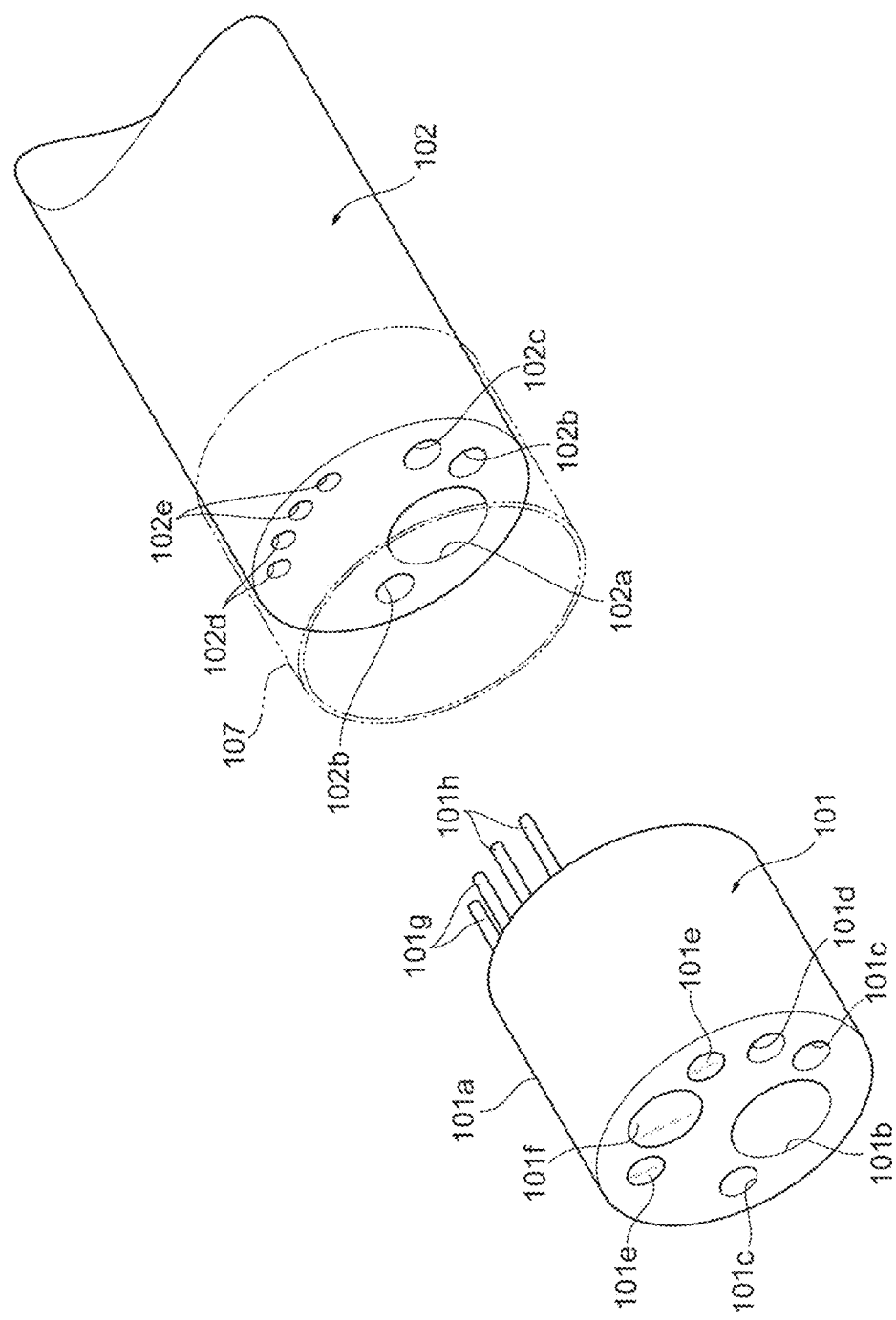
FIG. 4 is a perspective view illustrating a relationship between the distal end portion 101 and a curved portion 102 of the endoscope 10 according to the embodiment.

FIG. 4 is a perspective view illustrating a relationship between the distal end portion 101 and the curved portion 102 of the endoscope 10 according to the embodiment. In FIG. 4, the curved portion 102 includes a forceps port 102a, an air supply port/water supply port 102b, and a water jet port 102c at a distal end. The forceps port 102a, the air supply port/water supply port 102b, and the water jet port 102c are respectively a plurality of channels provided to the curved portion 102, i.e., openings at end portions of a forceps channel, air supply/water supply channels, and a water jet channel.

The curved portion 102 includes a power supply connector 102d and a signal connector 102e of a contact scheme at a distal end. The power supply connector 102d is connected with, for example, a power supply terminal of the connector portion 106 via a power supply cable inserted in the cable channels of the soft portion 103 and the curved portion 102. The signal connector 102e is connected with, for example, a signal terminal of the connector portion 106 via a signal cable inserted in the cable channels of the soft portion 103 and the curved portion 102.

The distal end portion 101 includes a main body portion 101a of a cylindrical shape, a forceps port 101b which is provided to the main body portion 101a, an air supply port/water supply port 101c, a water jet port 101d, an LED light 101e, and an imaging element 101f. Furthermore, the distal end portion 101 includes a power supply terminal (power supply pin) 101g and a signal terminal (signal pin) 101h at a rear end of the main body portion 101a connected with the distal end of the curved portion 102. The power supply terminal 101g is connected with, for example, the LED light 101e and the imaging element 101f. By inserting and connecting the power supply terminal 101g in and to the power supply connector 102d at the distal end of the curved portion 102, it is possible to supply power to the LED light 101e and the imaging element 101f.

The signal pin 101h is connected with, for example, the imaging element 101f. By inserting and connecting the signal pin 101h in and to the signal connector 102e at the distal end of the curved portion 102, it is possible to output an image signal of the imaging element 101f to the signal terminal of the connector portion 106 via the signal cable. In addition, connection for outputting the image signal of the imaging element 101f can be also changed to, for example, radio connection such as Bluetooth (registered trademark).

A coupling portion of the distal end portion 101 and the curved portion 102 is covered by a fractured portion 107 of a tube shape. A resin having softness and flexibility can be used as a material of the fractured portion 107 similar to, for example, the resin which forms the curved portion 102 and the soft portion 103. The fractured portion 107 covers not only the coupling portion of the distal end portion 101 and the curved portion 102, and, for example, a rear end portion of the main body portion 101a of the distal end portion 101 adjacent to the coupling portion, and the distal end portion of the curved portion 102. The fractured portion 107 is adhered or coupled to, for example, the rear end portion of the distal end portion 101 and the distal end portion of the curved portion 102, and is fractured when the distal end portion 101 is detached from the curved portion 102.

The endoscope 10 according to the present embodiment can prevent a third party without an authority from detaching the distal end portion 101 by the fractured portion 107. If the distal end portion 101 is detached from the curved portion 102, the fractured portion 107 is fractured, so that it is possible to easily decide that the distal end portion 101 has been detached.

Relationship Between Distal End Portion and Curved Portion of Endoscope (Modified Example 1)

Figure 5B:
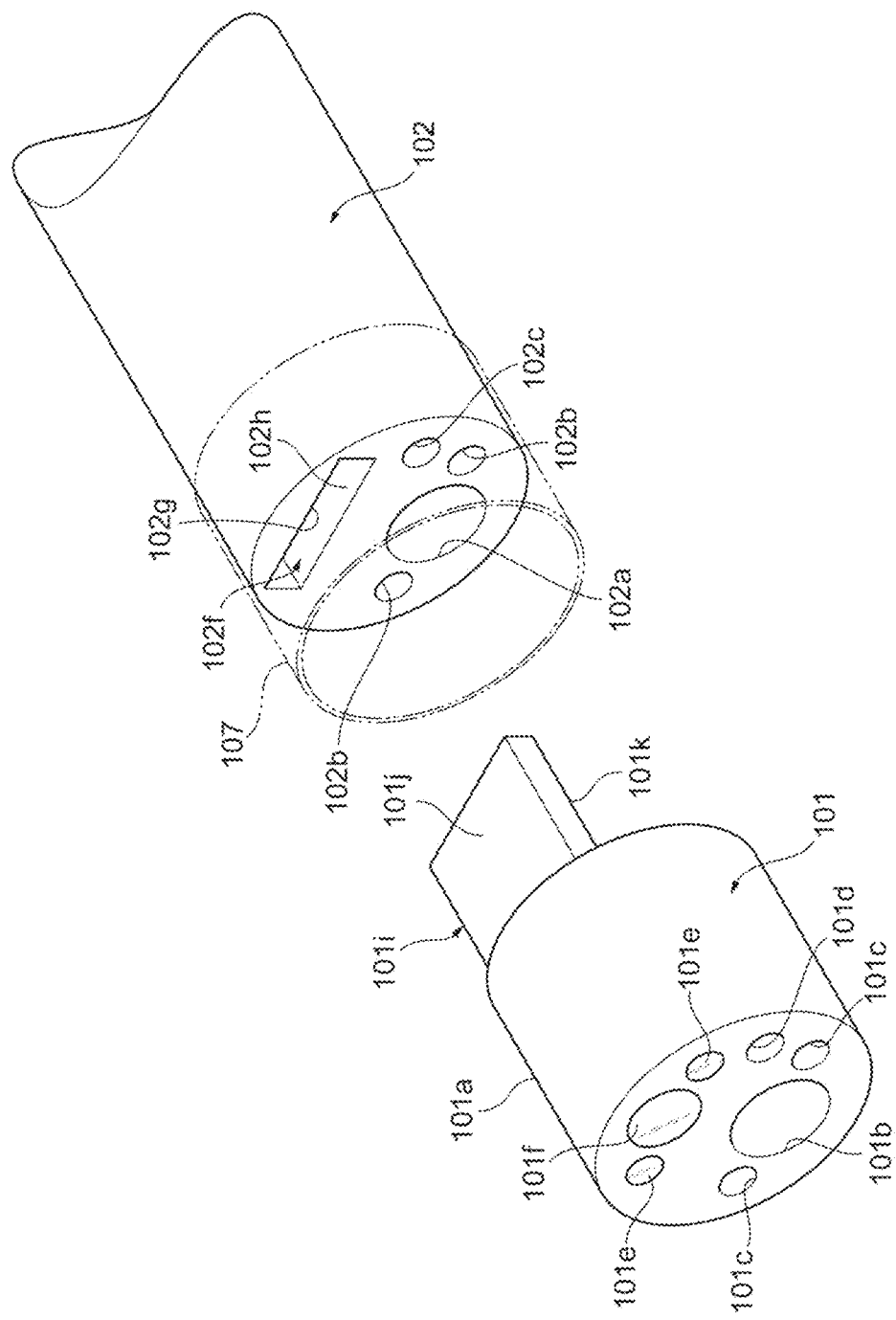
FIG. 5B is a cross-sectional view illustrating the relationship between the distal end portion 101 and the curved portion 102 of the endoscope according to modified example 1.

FIG. 5A is a cross-sectional view illustrating the relationship between the distal end portion 101 and the curved portion 102 of the endoscope according to modified example 1. FIG. 5B is a perspective view illustrating the relationship between the distal end portion 101 and the curved portion 102 of the endoscope according to modified example 1. Modified example 1 discloses one example of a case where power is transmitted to the distal end portion 101 by a planar electrode connector scheme.

According to modified example 1, the distal end portion 101 includes a protrusion portion 101i of a flat plate shape which protrudes rearward from a rear end of the main body portion 101a. The protrusion portion 101i of the flat plate shape includes one surface on which a positive electrode 101k is formed, and the other surface on which a negative electrode 101j is formed. The positive electrode 101k and the negative electrode 101j are respectively connected with the imaging element 101f.

The curved portion 102 includes a recess portion 102f which allows insertion of the protrusion portion 101i of the distal end portion 101 at the distal end. When the protrusion portion 101i of the distal end portion 101 is inserted in the recess portion 102f, a positive electrode 102h is formed on one surface of the recess portion 102f facing the positive electrode 101k of the distal end portion 101. Furthermore, when the protrusion portion 101i of the distal end portion 101 is inserted in the recess portion 102f, a negative electrode 102g is formed on the other surface of the recess portion 102f facing the negative electrode 101j of the distal end portion 101.

According to modified example 1, it is possible to transmit power from the positive electrode 102h and the negative electrode 102g of the curved portion 102 to the positive electrode 101k and the negative electrode 101j of the distal end portion 101 by a planar electrode port connector scheme, and supply power to the imaging element 101f.

Relationship Between Distal End Portion and Curved Portion of Endoscope (Modified Example 2)

Figure 6A:
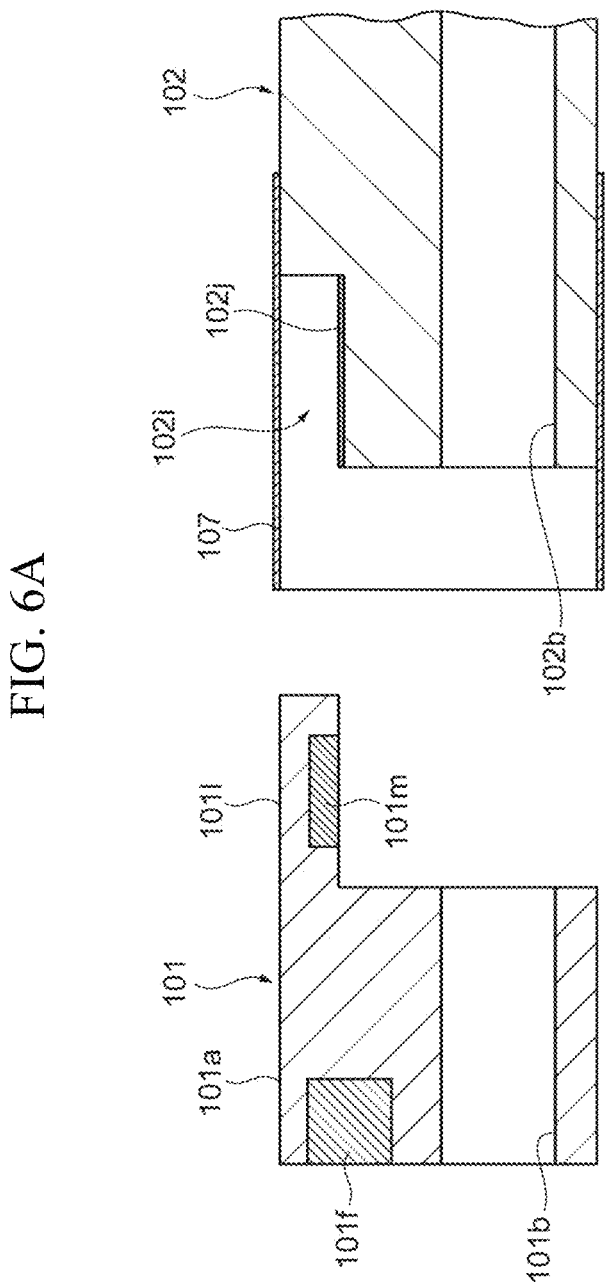
FIG. 6A is a cross-sectional view illustrating the relationship between the distal end portion 101 and the curved portion 102 of the endoscope according to modified example 2.
Figure 7A:
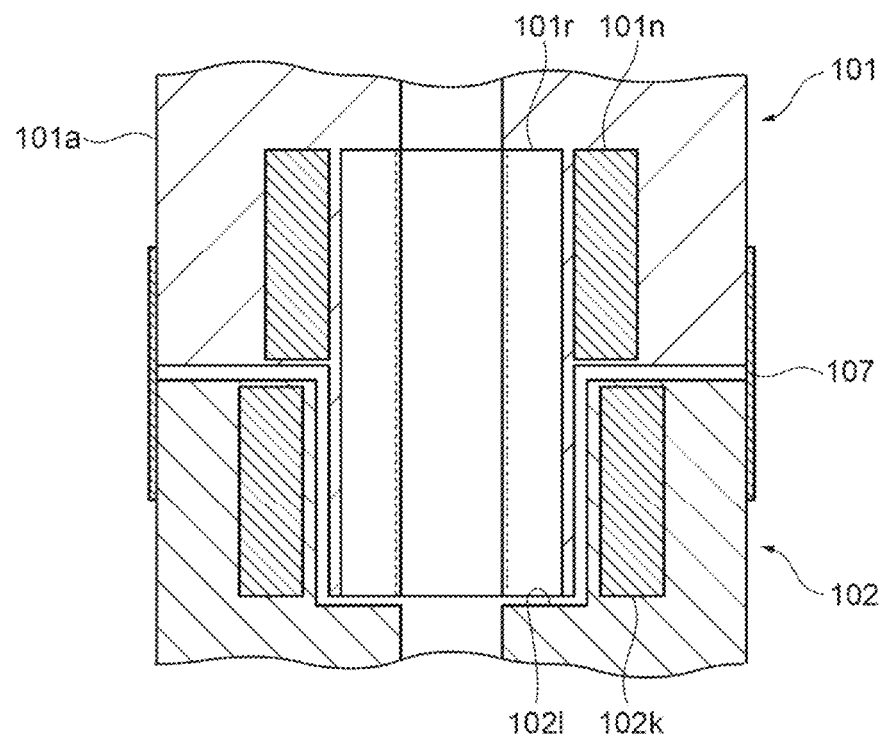
FIG. 7A is a cross-sectional view (1) illustrating the relationship between the distal end portion 101 and the curved portion 102 of the endoscope 10 according to modified example 3.
Figure 7B:
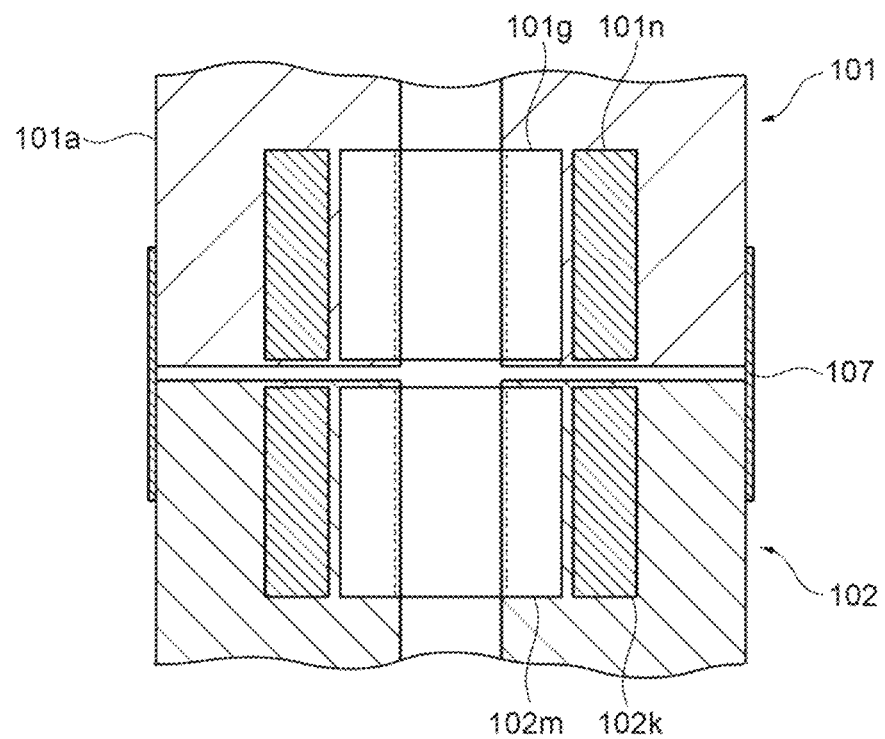
FIG. 7B is a cross-sectional view (2) illustrating the relationship between the distal end portion 101 and the curved portion 102 of the endoscope 10 according to modified example 3.
Figure 7C:
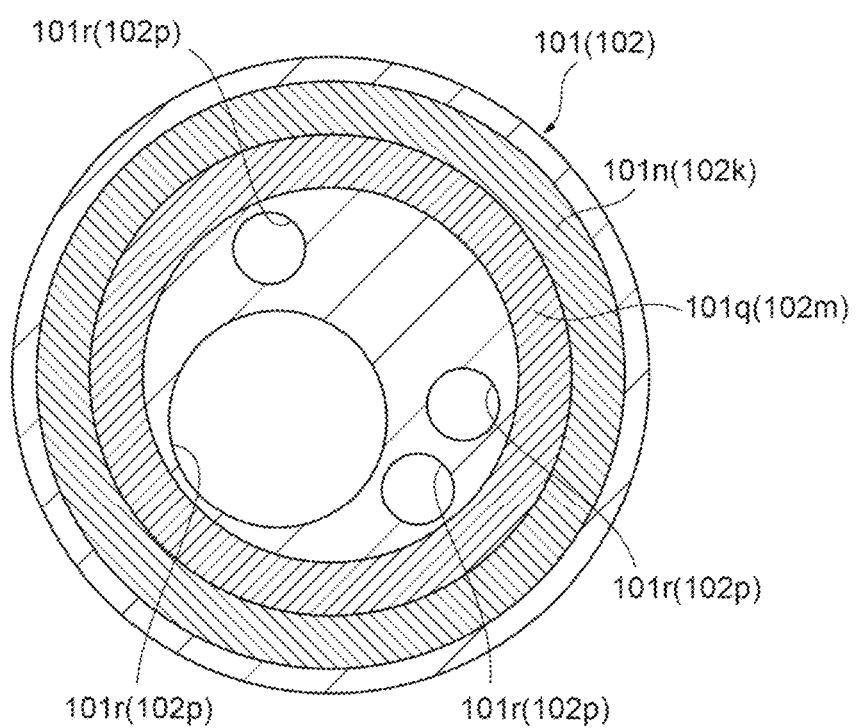
FIG. 7C is a cross-sectional view (3) illustrating the relationship between the distal end portion 101 and the curved portion 102 of the endoscope 10 according to modified example 3.
Figure 7D:
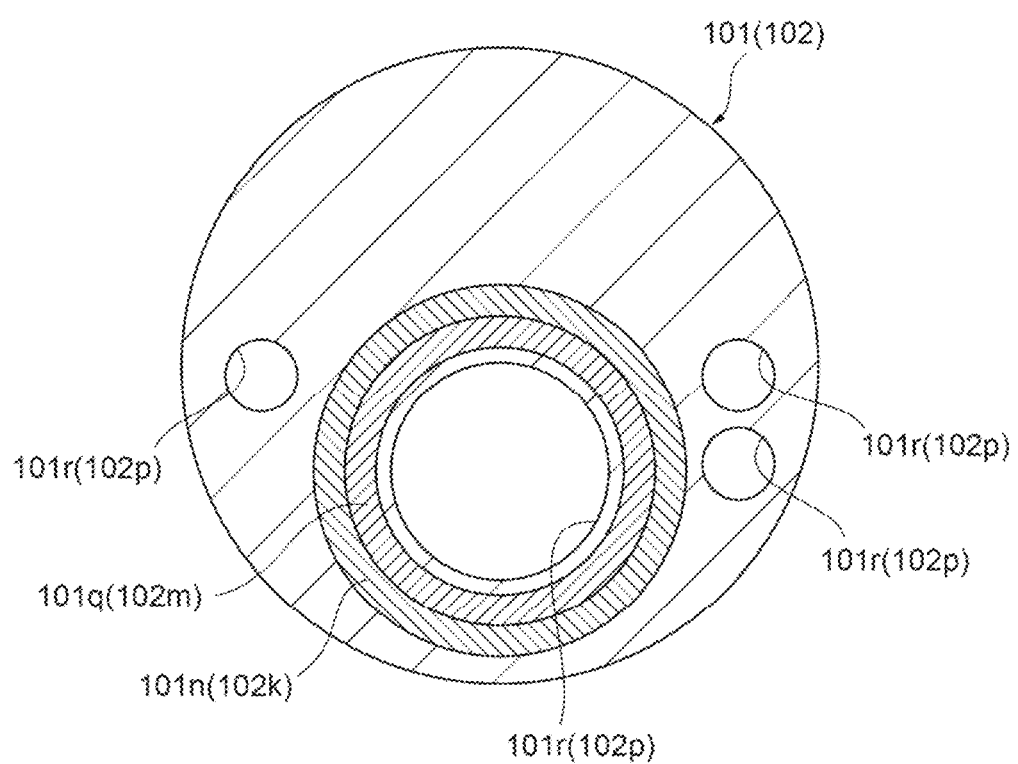
FIG. 7D is a cross-sectional view (4) illustrating the relationship between the distal end portion 101 and the curved portion 102 of the endoscope 10 according to modified example 3.

FIG. 6A is a cross-sectional view illustrating the relationship between the distal end portion 101 of the endoscope and the curved portion 102 according to modified example 2. FIG. 6B is a perspective view illustrating the relationship with the curved portion 102 of the endoscope according to modified example 2. Modified example 2 discloses an example of a case where power is transmitted to the distal end portion 101 by a two-dimensional communication scheme (evanescent wave scheme).

Relationship Between Distal End Portion and Curved Portion of Endoscope (Modified Example 3)

FIGS. 7A to 7D are cross-sectional views illustrating the relationship between the distal end portion 101 and the curved portion 102 of the endoscope 10 according to modified example 3. Modified example 3 discloses an example of a case where power is transmitted to the distal end portion 101 by an electromagnetic induction scheme.

Relationship Between Distal End Portion and Curved Portion of Endoscope (Modified Example 4)

Figure 8A:
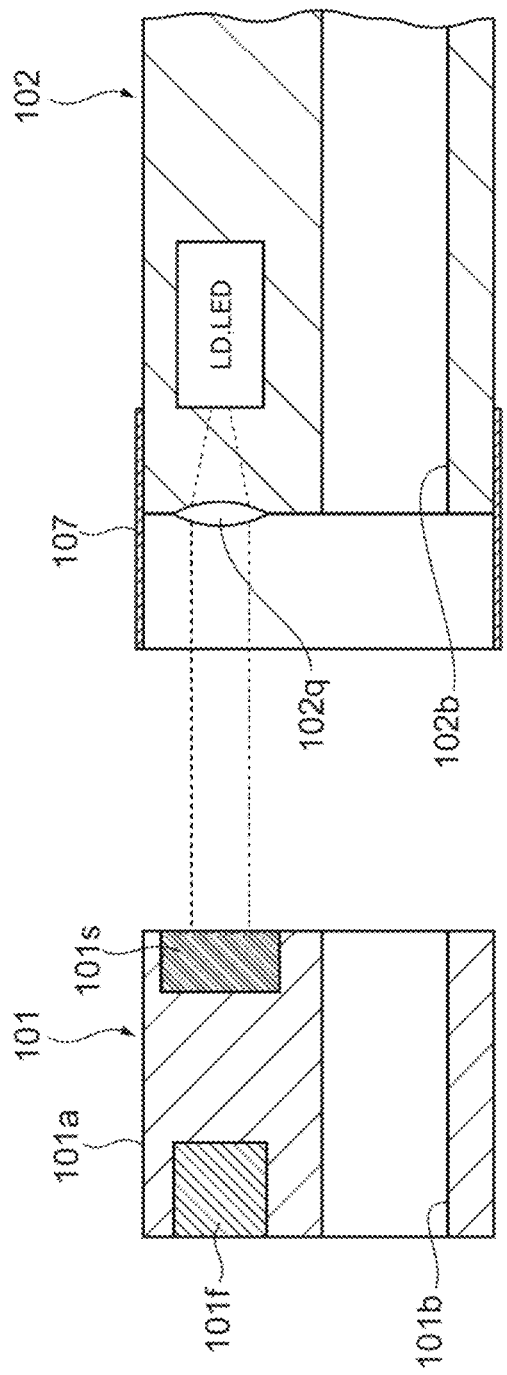
FIG. 8A is a cross-sectional view (1) illustrating the relationship between the distal end portion 101 and the curved portion 102 of the endoscope 10 according to modified example 4.
Figure 8B:
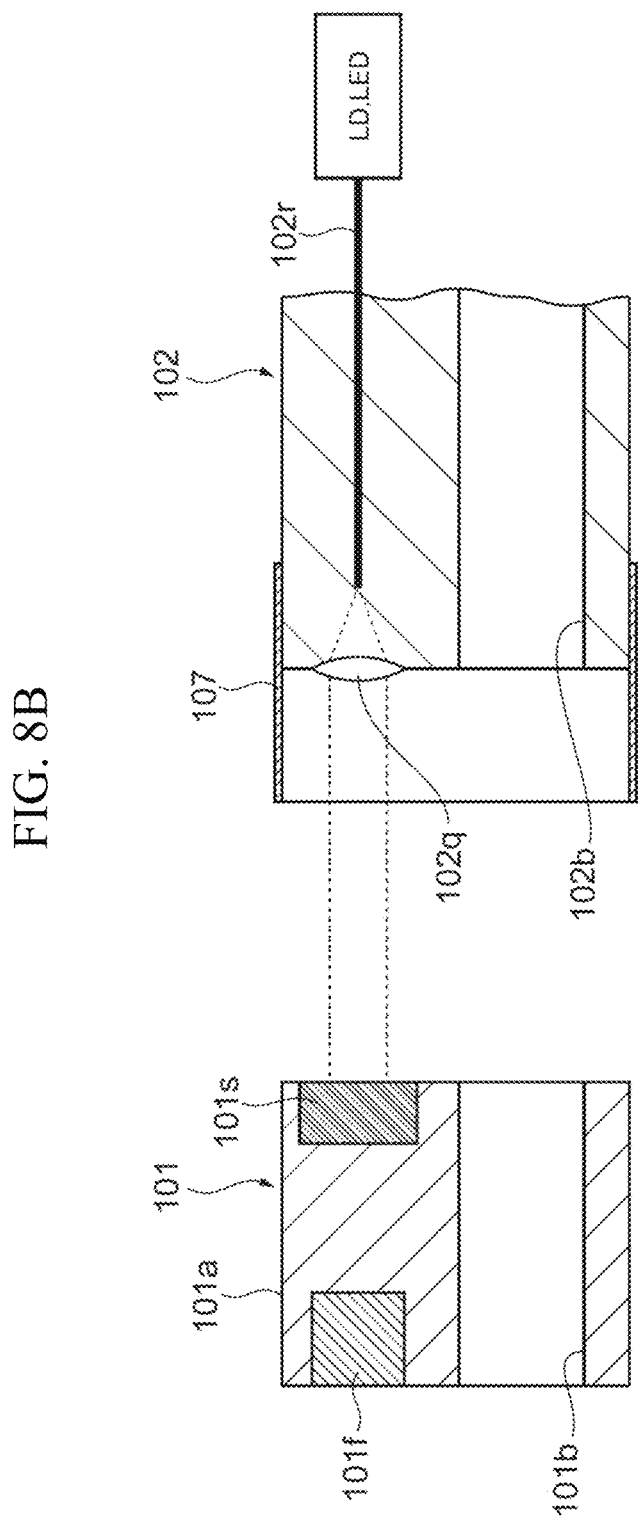
FIG. 8B is a cross-sectional view (2) illustrating the relationship between the distal end portion 101 and the curved portion 102 of the endoscope 10 according to modified example 4.

FIGS. 8A and 8B are cross-sectional views illustrating the relationship between the distal end portion 101 and curved portion 102 of the endoscope 10 according to modified example 4. Modified example 4 discloses an example of a case where power or a signal is transmitted by an optical transmission scheme.

Relationship Between Distal End Portion and Curved Portion of Endoscope (Modified Example 5)

Figure 9:
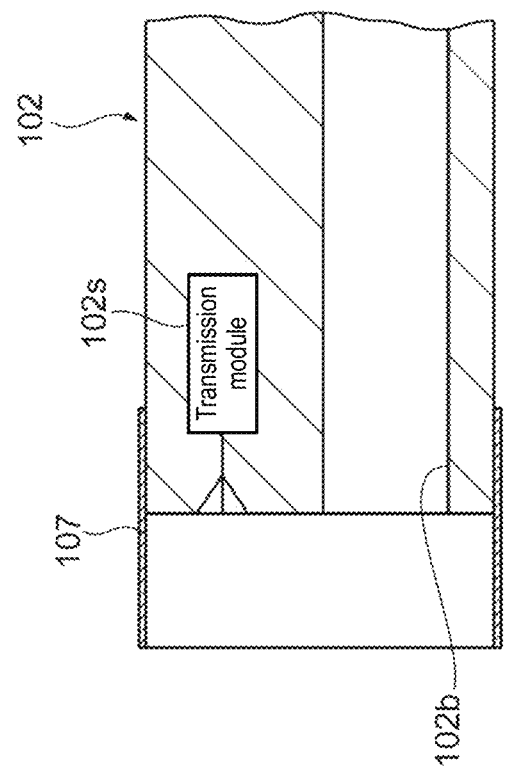
FIG. 9 is a cross-sectional view illustrating the relationship between the distal end portion 101 and the curved portion 102 of the endoscope 10 according to modified example 5.
Figure 9:
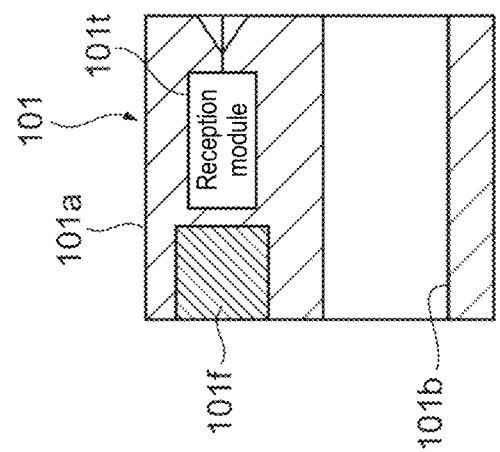

FIG. 9 is a cross-sectional view illustrating the relationship between the distal end portion 101 and the curved portion 102 of the endoscope 10 according to modified example 5. Modified example 5 discloses an example of a case where power or a signal is transmitted by a wireless transmission scheme.

Another Aspect of Distal End Portion of Endoscope (Modified Example 6)

Figure 10:
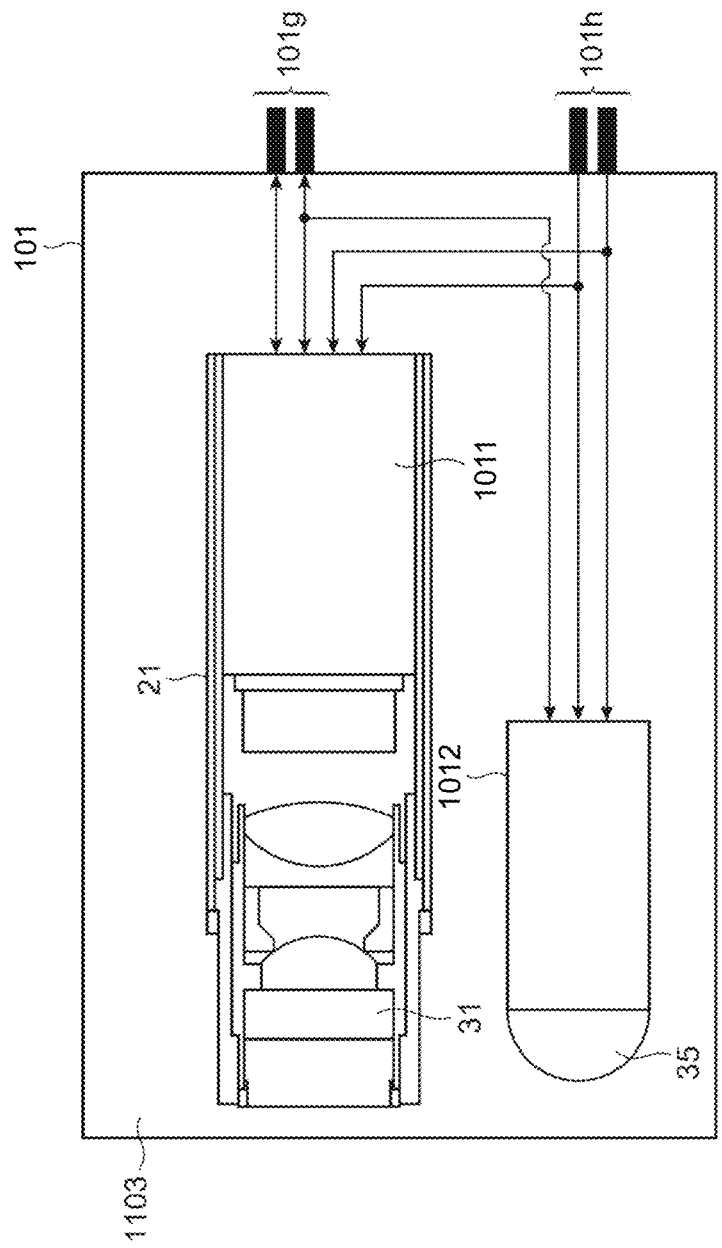
FIG. 10 is a view illustrating a cross-sectional configuration of the distal end portion 101 of the endoscope 10 according to another aspect (modified example 6).

FIG. 10 is a view illustrating a cross-sectional configuration of the distal end portion 101 of the endoscope 10 according to another aspect (modified example 6). The above embodiment and modified examples 1 to 5 have described a configuration in a case where the distal end portion 101 itself is reused. However, at least the imaging unit 21 (or only the imaging element) included in the distal end portion 101 may be taken out from the distal end portion 101, and reused. In addition, the imaging element and the small LED light may be taken out and reused.

As illustrated in FIG. 10, the distal end portion 101 of the endoscope 10 includes the imaging unit 21 which includes an imaging element 1011 and the objective lens 31, a small LED light 1012 which includes the lens 35, a power supply terminal (e.g., pin contact point) 101g which supplies power to the imaging unit 21 and the small LED light 1012, and a signal terminal (e.g., pin contact point) 101h which supplies a control signal to the imaging unit 21 and the small LED light 1012, and outputs an image signal from the imaging unit 21, and is formed with these components covered and housed by a housing 1013. The housing 1013 is formed by, for example, a resin (e.g., a resin different from the resin used for the curved portion 102), so that it is possible to destroy the housing 1013 to peel the surfaces covering the components, and easily take out the housed imaging unit 21 and small LED light 1012. Furthermore, it is possible to reuse the imaging unit 21 (only the imaging element 1011 depending on cases) and the small LED light 1012 which have been taken out. Connection between a power supply line and a signal line extending from the power supply terminal 101g and the signal terminal 101h, and the imaging unit 21 and the small LED light 1012 is not limited to, for example, a method such as solder, and may be established by a method which can easily take out the imaging unit 21 and the small LED light 1012. By, for example, performing pressure bonding or pressure welding or by using a conductive zebra (a reliable pressure-contact type connector in which a conductive silicone rubber whose conductors are metal particles, and an insulation silicone rubber are alternately aligned and enables random connection), it is possible to disassemble wire connection.

<Distribution Model of Single Use Endoscope>

All portions of the single use endoscope 10 according to the present embodiment are not single-use, and the distal end portion 101 or the imaging unit 21 and the small LED light (a case where an illumination unit is built-in the distal end portion 101) included in the distal end portion 101 are reused. The following distribution model can be assumed for the single use endoscope 10.

For example, a video processor 20 and a monitor M1 in the endoscope system 1 are provided as a device (pay-per-use device) which is charged per use to the hospital side. Furthermore, for example, the N unused single use endoscopes 10 (an initial delivery number is determined based on a contract) are delivered to the hospital side. A unique identification number is given to each unused single use endoscope 10 (for example, an ID number is stored in a built-in memory (not illustrated) of the distal end portion 101), and a single use endoscope provider (e.g., manufacturer) and/or the hospital can manage the individual single use endoscope 10 by a computer.

When the user (operator) on the hospital side uses the single use endoscope 10, a specific identification number of the single use endoscope 10 is read by a reader, and is stored as the single use endoscope 10 used by the computer on the hospital side. Furthermore, information of the used endoscope 10 is transmitted to a computer of the single use endoscope provider from the computer on the hospital side via the Internet, and is collectively managed therein.

The used single use endoscope 10 is strictly managed on the hospital side, is collected by a specific junk dealer at a certain cycle or every time the single use endoscope 10 is used, and is sent to the single use endoscope provider (or a disassembly/cleaning/reassembly operator).

The single use endoscope provider disassembles the collected and used single use endoscope 10, takes out only the distal end portion 101, and discards or incinerates other portions (the curved portion 102, the soft portion 103, the operation unit 104, the connector cable portion 105, and the connector portion 106). Furthermore, the provider can carefully clean, sterilize, and reuse the distal end portion 101. When only the imaging unit 21 included in the distal end portion 101 is reused, only the imaging unit 21 is taken out from a housing 1103 of the distal end portion 101 (the housing 1103 is broken and discarded), and the imaging unit 21 which has been taken out can be reused.

Subsequently, the provider uses the reusable distal end portion 101, the unused curved portion 102, soft portion 103, operation unit 104, connector cable portion 105, and connector portion 106, and the built-in cables to assemble the single use endoscope 10. In this case, the built-in memory (not illustrated) of the distal end portion 101 stores a unique identification number of the newly assembled single use endoscope 10.

The provider delivers the newly assembled single use endoscope 10 in, for example, the N units according to a use situation of the single use endoscope 10 on the hospital side. The hospital side pays a money amount charged according to the number of the actually used single use endoscopes 10 and the number of times of use of the video processor 20 in the endoscope system 1 (the number of the used single use endoscope 10 and the number of times of use of these devices can be also counted) to the single use endoscope provider. By repeating the above cycle, it is possible to achieve the distribution model of the single use endoscope 10 according to the present embodiment.

By providing the single use endoscope 10 according the above-described configuration and distribution model, it is possible to maintain a high cleaning level at all times, and realize endoscope inspection which can reduce a burden of cleaning. More specifically, a cleaning process of the endoscope in the hospital is unnecessary, so that it is possible to eliminate a burden related to cleaning on the hospital side (it is possible to provide human resources and materialistic resources for cleaning). Furthermore, failure repair and frequent inspection of the endoscope are not performed, and order processing of consumables for the endoscope (a cleaning brush, an 0 ring and a valve) becomes unnecessary, so that it is possible to reduce the burden related to management of the endoscope system on the hospital side. The video processor 20 to be repeatedly used is provided from the provider to the hospital and charged in use units, so that the hospital side does not need to make an initial investment and it is possible to reduce a cost burden on the hospital side, too. Furthermore, the new single use endoscope 10 is delivered from the provider to the hospital per predetermined period, so that the hospital side does not need to perform stock management and take an order procedure, and it is possible to reduce a hospital's burden related to the stock management and the order procedure, too. That is, this model can convert all expenses related to the single use endoscope 10 into variable cost matching the number of symptoms. Furthermore, all portions of the single use endoscope 10 are not single-use, and the relatively expensive distal end portion 101 or the expensive imaging element included in the distal end portion 101 or a light is reused, so that it is possible to realize the single use endoscope while suppressing cost without undermining quality of an image imaged by the endoscope.

Hydrophilic Coating (Modified Example 7)

Conventionally, there is a case where, when an endoscope is inserted in a body of a subject (patient), a flexible tube sticks to an intestine wall and is difficult to insert. Hence, an oil is coated on a flexible tube surface, air is supplied into an intestine of the subject, and the thickness of the intestine is expanded to allow insertion of the flexible tube. However, an endoscope device to be repeatedly used has a problem in terms of hygiene in a case of the former, and has a problem that the subject feels fullness in the abdomen and is uncomfortable in a case of the latter.

In this regard, the endoscope 10 according to the present embodiment is a single use (disposal) endoscope which does not need to take repetition of sterilization into account. Hence, according to the present embodiment, hydrophilic coating for lowering a friction factor is applied to a surface (at least part of the surface) of a flexible tube portion (the distal end portion 101+the curved portion 102+the soft portion 103) of the single use endoscope 10.

More specifically, it is necessary to apply hydrophilic coating which secures biological safety (guarantees biocompatibility). For example, a hyaluronic acid based hydrophilic coating material is used as the hydrophilic coating material for the hydrophilic coating. The hyaluronic acid based hydrophilic coating material is a coating material which has very good slipperiness and long-term durability, and is a material which is optimal to improve operability. Furthermore, the hyaluronic acid based hydrophilic coating material instantaneously exhibits the slipperiness when contacting a normal saline, a blood or a body fluid, and has a good initial sliding property, too. Furthermore, the hyaluronic acid based hydrophilic coating material is a material whose cytotoxicity, hemolysis, systemic toxicity, intradermal reaction, and thrombotic property are confirmed by a biological safety test, and has been registered in an FDA master file. The hyaluronic acid based hydrophilic coating material is a material which supports EOG sterilization, electron beam sterilization, gamma sterilization, and autoclave sterilization. In addition to the hyaluronic acid, PTFE/PEEK and a paraxylene polymer which reduce a frictional resistance and make it possible to easily access a periphery are also applicable as hydrophilic coating materials.

Although a protein or an oil generally adheres to and contaminates the hydrophilic coating, the hydrophilic coating is used only once for one patient, and therefore there is not a problem even if the hydrophilic coating is contaminated. Furthermore, the single use endoscope 10 is used by the specification in a short period of time (several hours at maximum), is not placed inside a body, and therefore is not requested to suppress cell proliferation and provide an antibacterial property. Furthermore, the single use endoscope 10 is single-use (disposal), and therefore durability and persistence are not important performance items.

Treatment Tool Function (Modified Example 8)

A treatment tool (e.g., an electric knife) used for Endoscopic Submucosal Dissection (ESD) is inserted through a forceps port of an endoscope device, and is discarded after use. However, a unit price of the treatment tool to be discarded is relatively expensive. On the other hand, the single use endoscope 10 is also discarded after use. The inventors of this application have thought that it is possible to reduce total cost by including a function of a single use treatment tool in the single use endoscope 10 in view of such a situation. The total cost is the substantially same as that of a product formed by adding an observation function to the treatment tool in terms of a price ratio, and a user can make single use without hesitation (without caring about cost).

Figure 11:
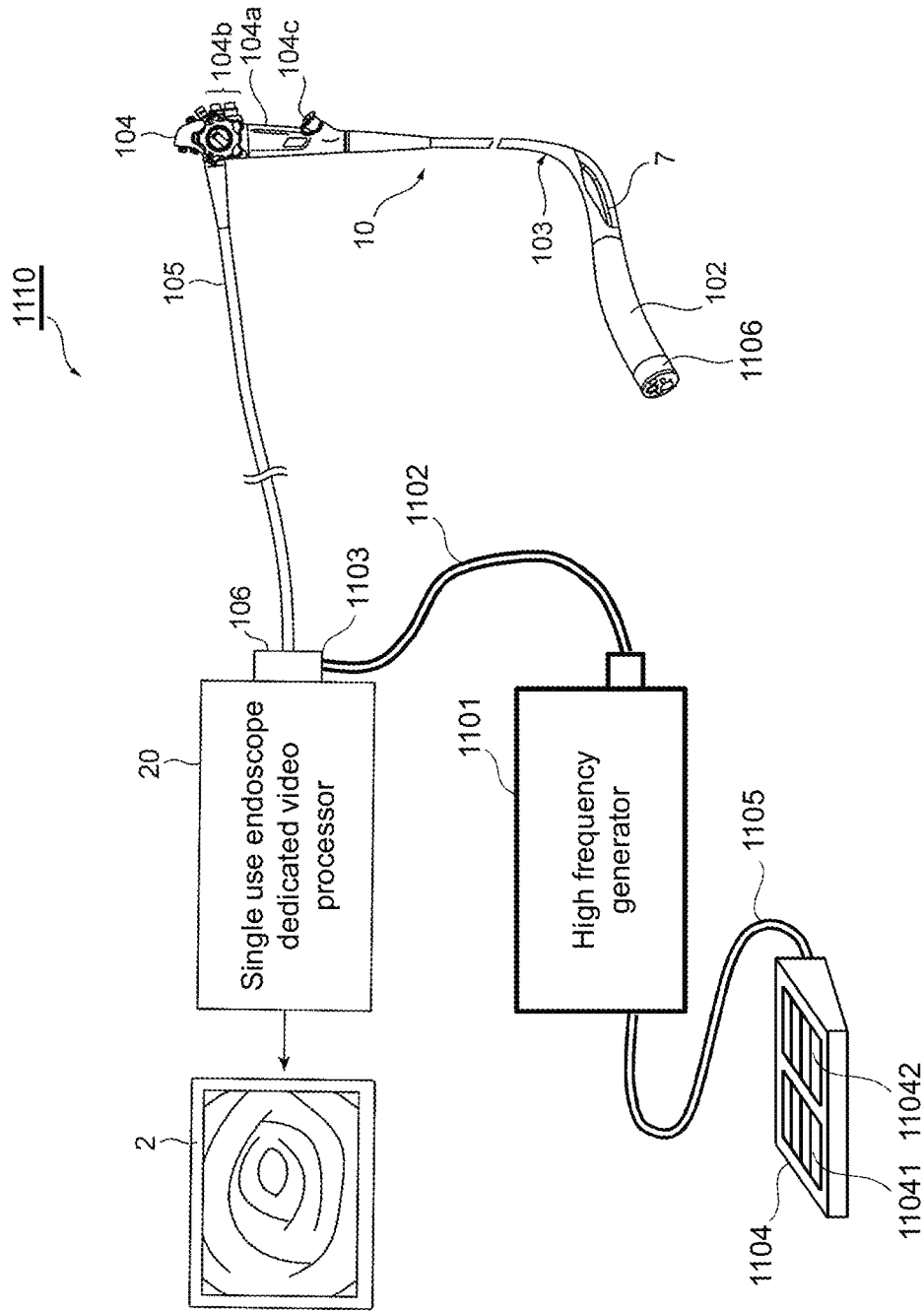
FIG. 11 is a view illustrating a schematic configuration example of an endoscope system 1110 with a treatment tool function according to modified example 8.

FIG. 11 is a view illustrating a schematic configuration example of an endoscope system 1110 with a treatment tool function according to modified example 8. The endoscope system 1110 with the treatment tool function includes, for example, the configuration in FIG. 1 and, in addition, a high frequency generator 1101 which supplies a high frequency current to a treatment tool (e.g., electric knife) provided at the distal end portion of the endoscope 10, the cable portion 1102 which connects the high frequency generator 1101 and the connector portion 106 at a connection portion 1102, a foot switch 1104 which includes a first switch 11041 which instructs the high frequency generator 1101 to output an incision continuous wave, and a second switch 11042 which instructs the high frequency generator 1101 to output a coagulation burst wave, and a cable 1105 which connects the foot switch 1104 and the high frequency generator 1101. In addition, a distal end portion 1106 of the single use endoscope system 1110 includes a treatment tool function unlike the distal end portion 101 of the single use endoscope 10 in FIG. 1. In addition, in replace of the foot switch, the operation unit 104 may be provided with an operation button (switch) and manually operated to instruct the high frequency generator 1101 to output the incision continuous wave or the coagulation burst wave or block a high frequency current.

Figure 12:
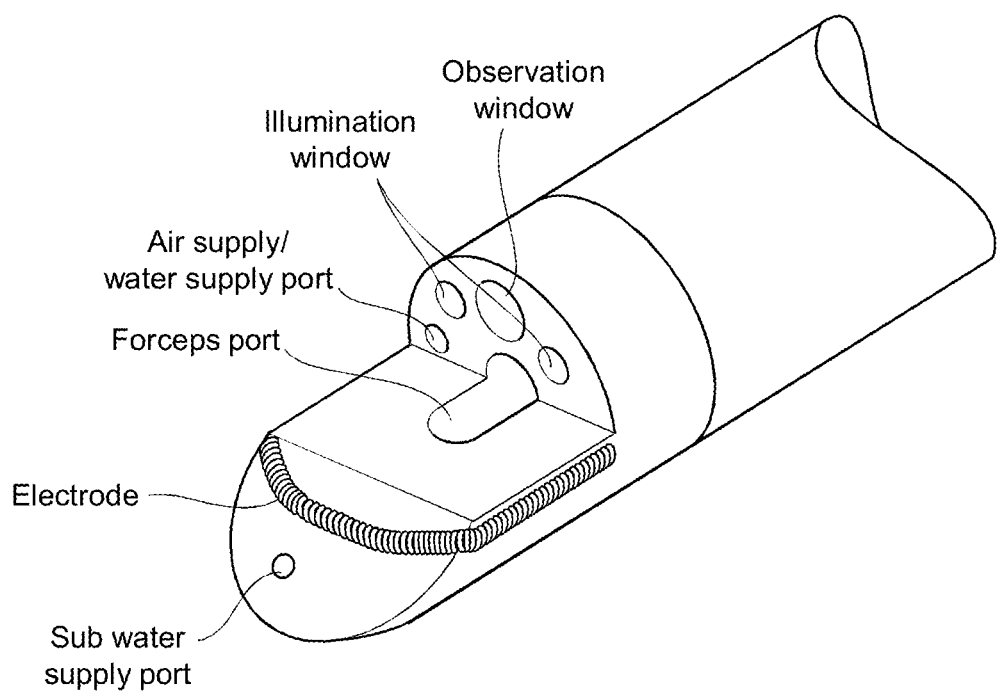
FIG. 12 is a view illustrating a configuration example of a distal end portion 1106 including a treatment tool of a monopolar mode.
Figure 13:
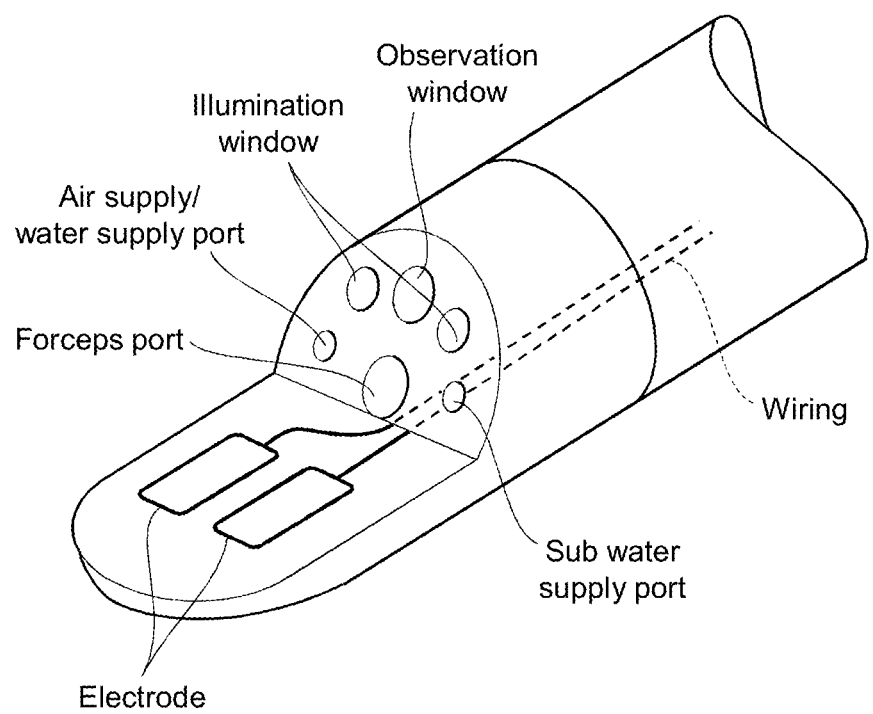
FIG. 13 is a view illustrating a configuration example of the distal end portion 1106 including the treatment tool of a bipolar mode.

By using, for example, a bipolar/monopolar electrosurgical high frequency generator as the high frequency generator 1101, it is possible to use the treatment tool in a bipolar mode or a monopolar mode. FIG. 12 is a view illustrating a configuration example of the distal end portion 1106 including the treatment tool of the monopolar mode. FIG. 13 is a view illustrating a configuration example of the distal end portion 1106 including the treatment tool of the bipolar mode.

In a case of the treatment tool of any mode, too, the treatment tool and the high frequency generator 1101 are connected by a power supply line which passes inside the single use endoscope system 1110.

In a case of the monopolar mode, as illustrated in FIG. 12, the distal end portion 1106 includes, for example, a monopolar electrode, an observation window for observing a portion at which the electrode and a tissue of a subject contact, an imaging element (CMOS) which is located at the depth of the observation window, and an illumination element (LED) for observation. In addition, when the single use endoscope system 1110 is used in the monopolar mode, a ground pad (a return electrode is inserted in the back of the subject) is used for the subject.

In a case of the bipolar mode, as illustrated in FIG. 13, the distal end portion 1106 includes a plurality of electrodes (a positive electrode and a negative electrode), an observation window for observing a portion at which the electrodes and a tissue contact, an imaging element (CMOS) which is located at the depth of the observation window, and an illumination element (LED) for observation. When the bipolar mode is used, the one electrode is connected with the one electrode of the two electrodes of the high frequency generator, and the other electrode is electrically connected with the other polarity of the two electrodes of the high frequency generator.

An electrode portion of the treatment tool of any mode may be configured to be movable. It is possible to adopt, for example, a mechanism which makes the electrode portion protrude forward compared to the distal end surface. Furthermore, there may be provided a water jet (sub water supply port) even in any mode to clean a treatment portion and cause a bleeding blood to flow. Furthermore, a forceps port is not limited to the positions illustrated in FIGS. 12 and 13. For example, the forceps port is formed at such a position that a liquid such as the blood can be easily suctioned.

An observation portion is configured to be direct viewing (the case of the monopolar mode: FIG. 12), and oblique viewing (bipolar mode: FIG. 13). Furthermore, when an esophageal wall is ablated, the observation portion may be configured to be lateral viewing in any mode.

Integration of Insertion Portion by Resin (Modified Example 9)

According to the present embodiment, as described above, a portion corresponding to a nozzle (an air supply nozzle or a water supply nozzle) or an illumination lens may be integrally molded with the distal end portion 101 by a resin. This integration molding realizes a cheap and disposable insertion portion.

Figure 14:
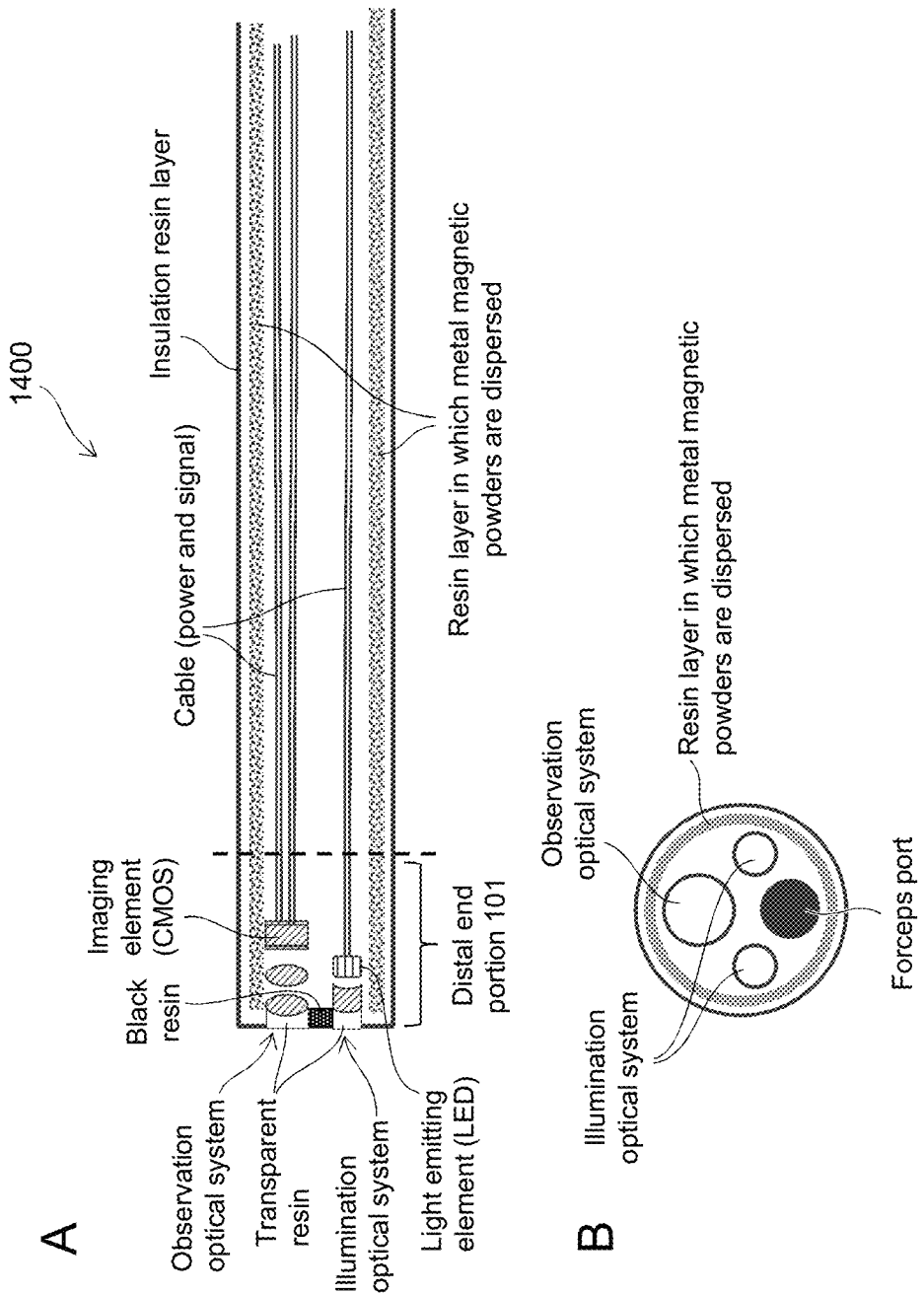
FIG. 14 is a view illustrating a configuration example of an insertion portion (the distal end portion 101+the curved portion 102+a soft portion 103) 1400 according to modified example 9.

FIG. 14 is a view illustrating a configuration example of an insertion portion (the distal end portion 101+the curved portion 102+the soft portion 103) 1400 according to modified example 9. FIG. 14A is a cross-sectional view in a longitudinal direction of the insertion portion, and FIG. 14B is a view illustrating a distal end front surface of the insertion portion.

The insertion portion 1400 includes an illumination optical system which illuminates a subject (object), a light source such as an LED for illumination, an observation optical system which forms a subject image, an imaging element (CMOS) which converts a formed optical image into an electrical signal, a resin portion which integrates cables for transmitting a power supply, a video signal and a control signal, and a resin layer (a resin layer in which metal magnetic powders are dispersed+an insulation resin layer) in which tube routes for supplying air and supplying water, and a forceps channel in which the treatment tool is inserted are also simultaneously molded inside the resin. The layer (the resin layer in which the metal magnetic powders are dispersed) is formed in part of the resin layer to taken an EMC countermeasure of the endoscope to absorb electromagnetic radiation noise from the cables and prevent the electromagnetic radiation noise from going outside. Furthermore, it is possible to increase a heat conductivity by the metal magnetic powders, and effectively transmit and dissipate heat from heat generating members such as the LED of the endoscope distal end portion and a CMOS imaging element.

As described above, by covering an entire surface of the insertion portion of the endoscope with the resin, it is possible to obtain a seamless complete water-proof structure. In addition, the resin to be used may be formed by bioplastic (biodegradable plastic) to prevent environmental contamination. Furthermore, a transparent resin which allows transmission of visible light is used for an optical portion, and a black resin may be used (e.g., multicolor molding is used) or a light shielding coating may be applied to prevent light of the illumination optical system from leaking to an observation optical system.

Modified Example of Fractured Portion (Modified Example 10)

According to modified example 4, there is provided the fractured portion 107 of a tube shape which covers the coupling portion of the distal end portion 101 and the curved portion 102 as described above (FIGS. 8A and B). However, modified example 10 will describe the fractured portion in a case where the insertion portion is integrally formed with the fractured portion similar to modified example 9.

The distal end portion 101 of the single use endoscope 10 (the same applies to the distal end portion 1106 of the single use endoscope 1100, too) detaches an imaging module which includes an illumination optical system which illuminates a subject (object), a light source such as an LED for illumination, an observation optical system which forms a subject image, and an imaging element which converts a formed optical image into an electrical signal, from an insertion portion at a junction portion which is connected with cables for transmitting a power supply, a video signal, and a control signal, and the imaging module is disassembled and detached at a factory to reuse. To make it possible to easily perform this disassembling/detaching operation, the insertion portion according to modified example 10 is provided with a decision portion near an installation position of the distal end portion of the integrally molded insertion portion.

Figure 15:
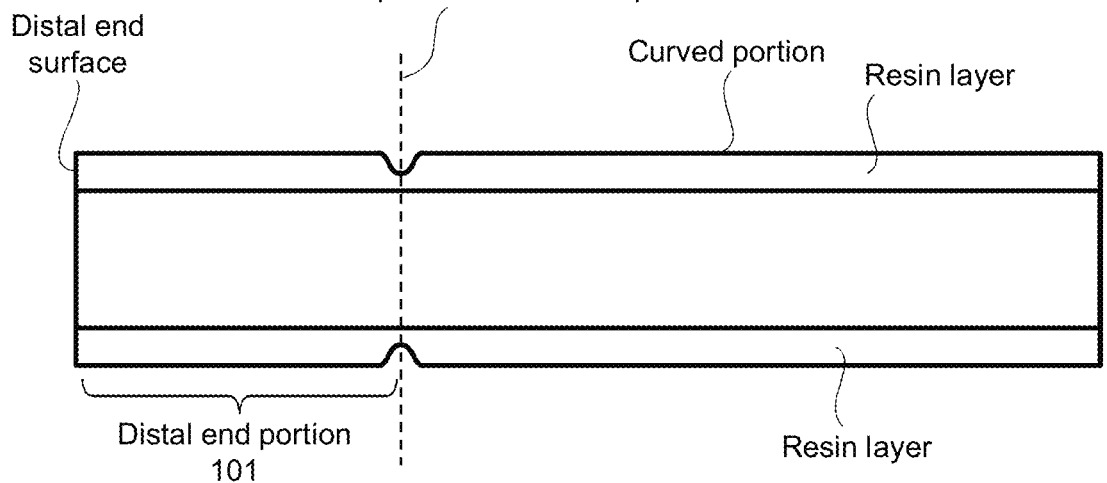
FIG. 15 is a view illustrating a cross section in the longitudinal direction of the insertion portion according to modified example 10.
Figure 15:
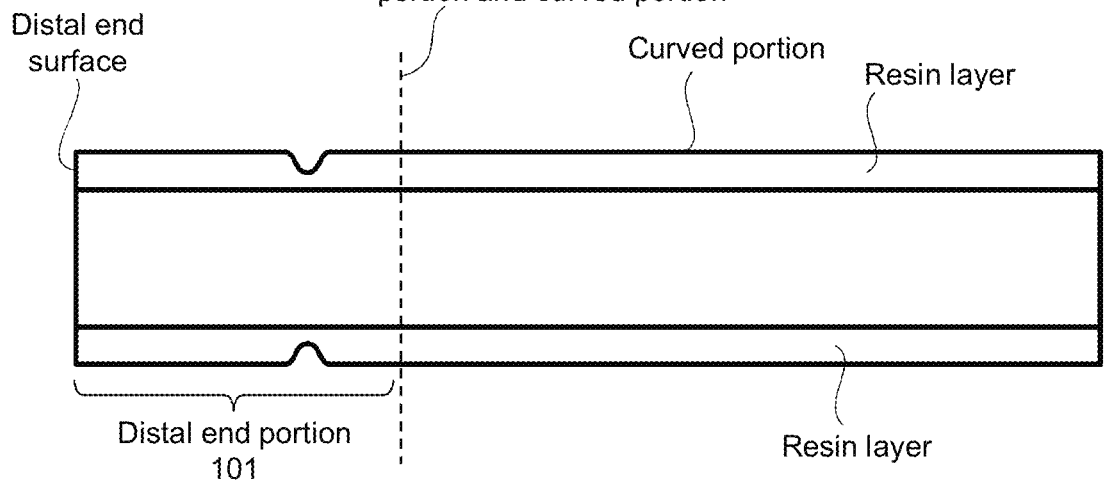
Figure 15:
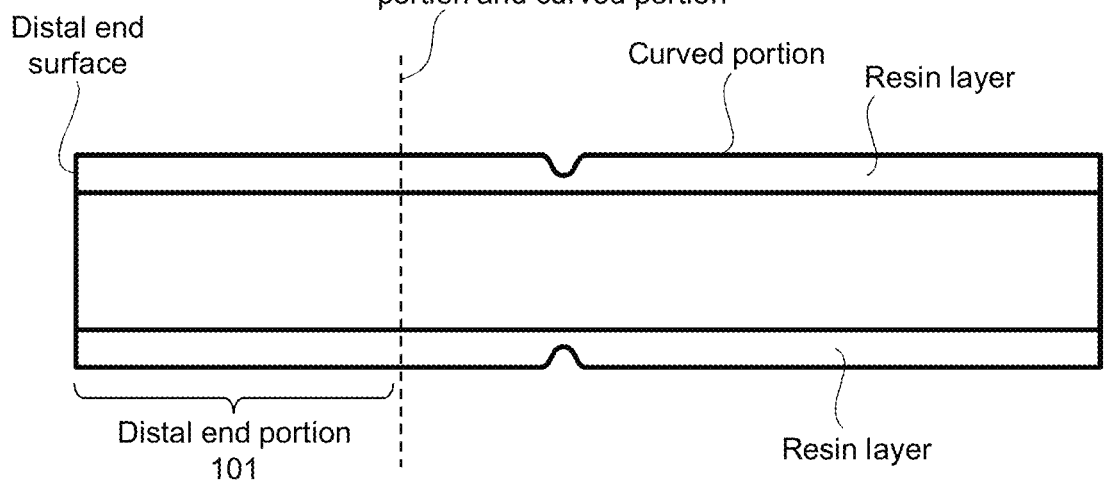

FIG. 15 is a view illustrating a cross-section in the longitudinal direction of the insertion portion according to modified example 10. FIG. 15 illustrates only a configuration of the fractured portion (a relationship between the resin layer of the fractured portion and the resin layer of the insertion portion other than the fractured portion), and omits a component such as the imaging module. As illustrated in FIG. 15, the thickness of the resin at any position (a position of the fractured portion) between the distal end surface of the insertion portion (the distal end of the distal end portion 101) and a predetermined position of the curved portion 102 is formed thinner than the thickness of the resin of the other portions. The thickness of the resin of a resin cutting position (the position of the fractured portion) is ¼ or more and ¾ or less and, more preferably, ⅓ or more and ½ or less than the thickness of the resin of the other portions. In this regard, a ratio of the thicknesses is a value which fluctuates according to hardness and strength of the resin used for integrally molding of the insertion portion. Furthermore, the fractured portion may be formed entirely or partially over a periphery of a side surface of the distal end portion 101. Furthermore, the position of the fractured portion (resin cutting position) can be set to such a position that a portion which is approximately ⅕ to ⅓ as the entirety of the distal end portion 101 is exposed from the entirety of the distal end portion 101. When the fractured portion is formed at the predetermined position of the curved portion 102 (any position closer to a side of the curved portion 102 than a boundary between the distal end portion 101 and the curved portion 102), the entirety of the distal end portion 101 is exposed. Furthermore, assuming that the imaging module is taken out by using a special jig, it is possible to provide the fractured portion at such a position that the exposed portion is further made smaller. Furthermore, colors of coating portions may be changed on an imaging module side and a flexible tube side to make it easy for a factory operator to distinguish a cutting point.

By forming the fractured portion according to the above configuration, the factory operator can easily and quickly take out the imaging module of the distal end portion 101, and reuse the imaging module which has been taken out.

Wireless Endoscope System (Modified Example 11)

Modified example 11 relates to a wireless endoscope which wirelessly transmits an image signal from an endoscope. In recent years, the endoscope is widely used in a medical field. In a case where inspection (observation) or a surgery is performed by using a conventional endoscope, it is necessary to supply power to an imaging element mounted on the endoscope, and connect with an external processor device of the endoscope a scope cable in which a signal line for transmitting a drive signal and an imaged signal is inserted, and is extended from the endoscope.

However, when the signal line in the scope cable is repeatedly bent beyond an assumed condition or disconnection occurs during use due to a failure, an operator needs to perform an operation matching the disconnection, and the operator feels stressful.

Hence, modified example 11 discloses the wireless endoscope which makes the scope cable (e.g., the connector cable portion 105 in FIG. 1) unnecessary, includes a battery (battery cell) mounted in the endoscope, and transmits a signal imaged by the imaging element wirelessly (by radio) to an outside.

Figure 16:
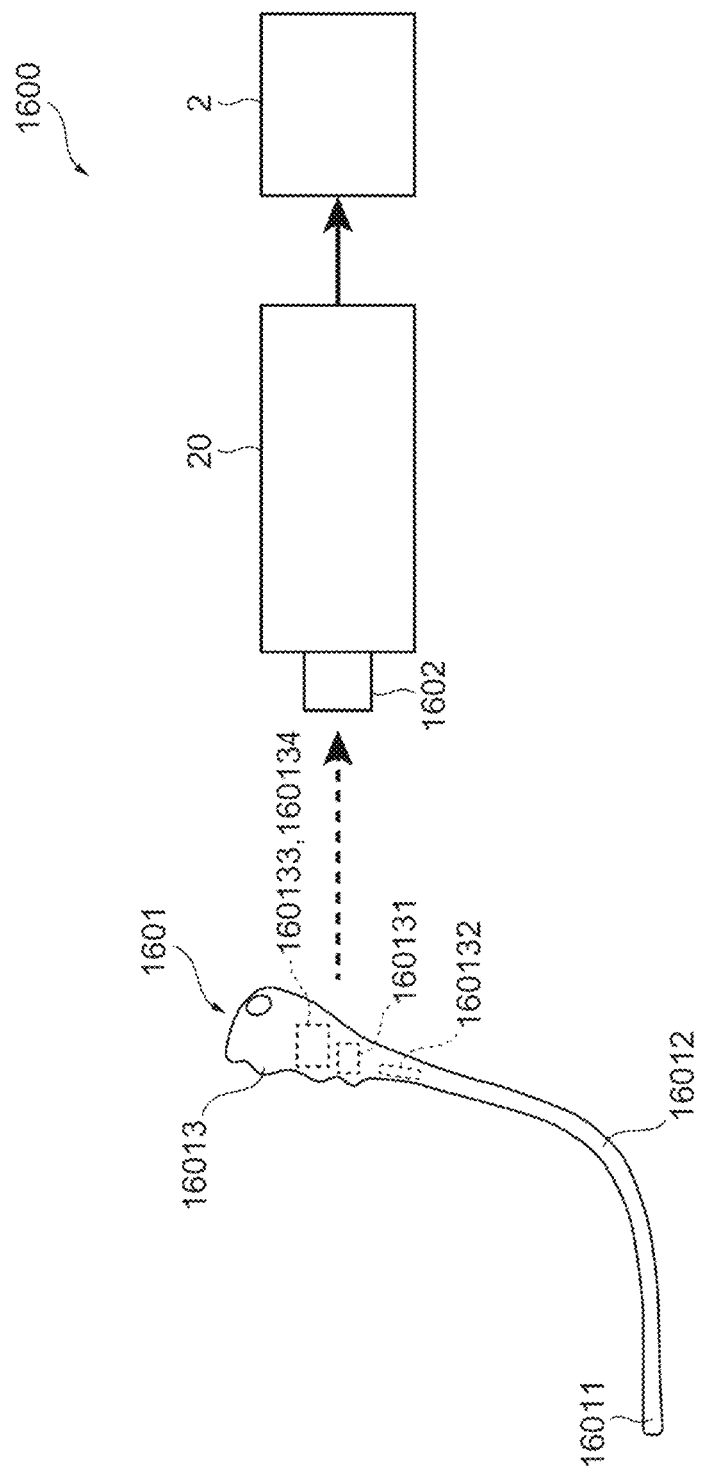
FIG. 16 is a view illustrating a schematic configuration of an endoscope system 1600 according to modified example 11.

FIG. 16 is a view illustrating a schematic configuration of an endoscope system 1600 according to modified example 11. The endoscope system 1600 includes an endoscope 1601, and the video processor (image display device) 20 which includes the monitor 2. The endoscope 1601 and the video processor 20 exchange data by using radio communication (a radio wave or an infrared ray). The video processor 20 functions as a signal processing device which receives an imaging signal transmitted by radio from the endoscope 1601, and generates a standard video signal (image signal). Furthermore, the monitor 2 receives the video signal generated by the video processor 20 via a metal cable, and displays an image corresponding to this video signal as an endoscope image on a display screen.

A main body of the endoscope 1601 includes a distal end portion 16011, an insertion portion 16012, and an operation unit 16013 which is formed at a rear end of the insertion portion 16012. An operation unit 1603 includes a battery 160131 which is detachably attached, a battery cell/power supply circuit 160132, a signal processing circuit 160133, and a transmission circuit 160134.

The distal end portion 16011 of the endoscope system 1600 includes an illumination light emitting diode (LED) 160111, an imaging optical system (objective lens) 160112, and an imaging element (a CMOS or a CCD) 160113 which is provided at an image forming position of the imaging optical system, and these components are appropriately disposed.

Figure 17:
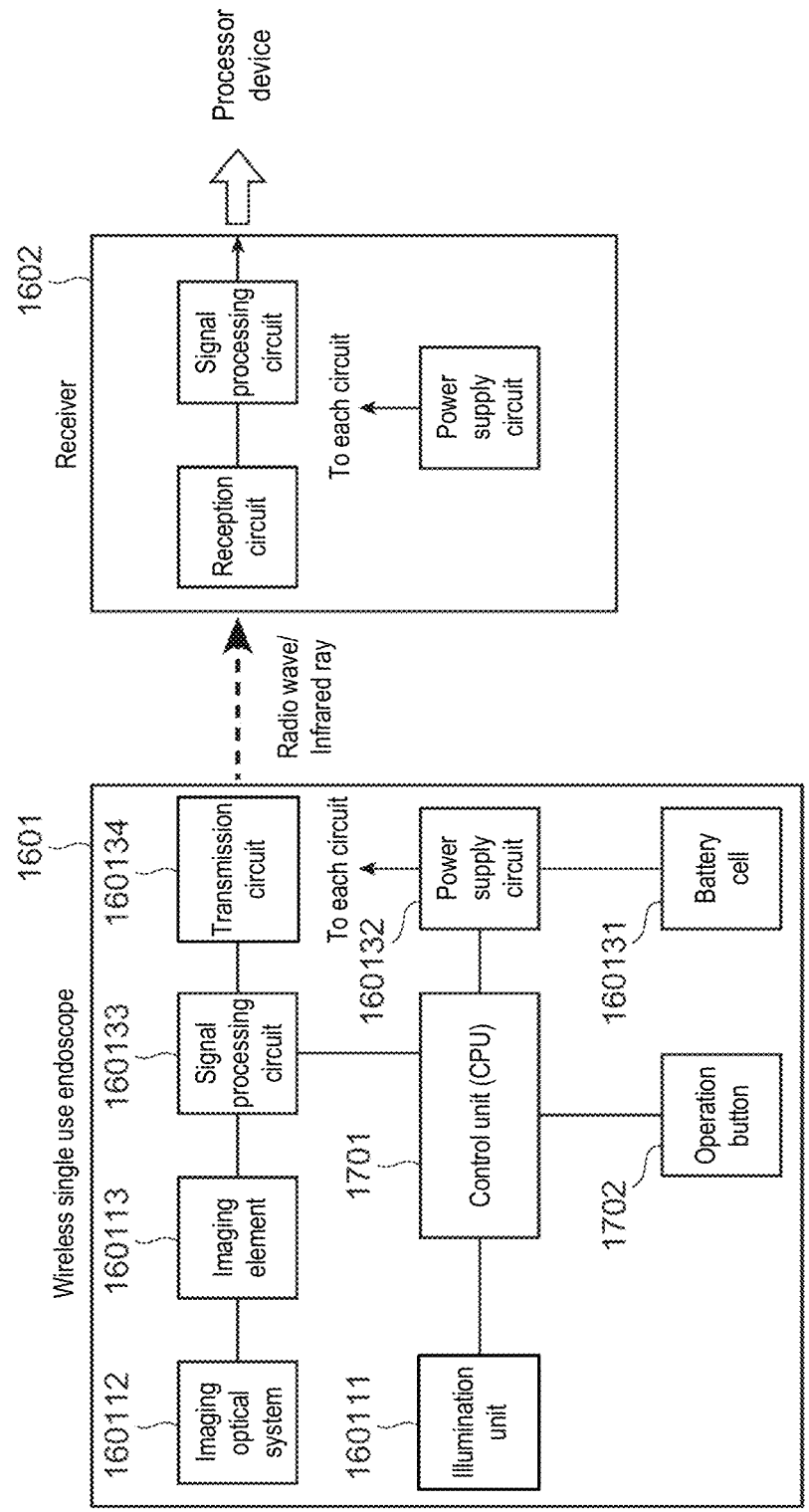
FIG. 17 is a view illustrating an internal circuit configuration of the endoscope system 1600 according to modified example 11.

FIG. 17 is a view illustrating an internal circuit configuration of the endoscope system 1600. The illumination light emitting diode (LED) 160111 is connected with a control unit (CPU) 1701 and the battery cell/power supply circuit 160132 which are provided inside the operation unit 16013 via a drive line which is disposed inside the insertion portion and causes light emission, and emits light when a drive signal supplied from the battery cell/power supply circuit 160132 is applied. The emitted light becomes illumination light which illuminates an interior of a body cavity in which the insertion portion 16012 is inserted through the distal end portion 16011.

The imaging optical system 160112 forms an optical image of the illuminated interior of the body cavity on an imaging plane of the imaging element 160113. The imaging element 160113 photoelectrically converts the formed optical image and generates an imaging signal. The signal processing circuit 160133 provided to the operation unit 16013 converts the imaging signal into a video signal to be transmitted. The transmission circuit 160134 modulates the generated video signal, and outputs the modulated video signal by radio (a radio wave/infrared ray) from an antenna (not illustrated) of the operation unit 16013. A receiver 1602 receives the video signal to pass to the video processor 20.

The wireless endoscope 1601 includes the insertion portion 16012 and the operation unit 16013, yet is not connected with the video processor 20 via a cable. Hence, the wireless endoscope system 1600 does not need a connector cable or a processor connection connector used for a general endoscope system.

The wireless endoscope 1601 includes the signal processing circuit 160133, a transmission circuit (wireless transmission circuit) 160134, and the battery 160131 built in the operation unit 16013, and part prices of these components are expensive. Hence, only the distal end portion 16011 and the insertion portion 16012 may be single-use, and the operation unit 16013 may be "reusable".

CONCLUSION

The embodiment of the present disclosure has been described in detail above. However, the present disclosure is not limited to the above embodiment, and enables various design changes without departing from the spirit of the present disclosure disclosed in the claims.

According to the above embodiment, after, for example, a single use endoscope device is used, the operation unit, the curved portion, the soft portion, the connector portion and the connector cable portion are discarded, and the distal end portion or at least the imaging element included in the distal end portion is reused. By so doing, it is possible to use an imaging unit having equal performance to that of an imaging unit used in a general endoscope (reuse type) as an imaging unit (at least the imaging element) included in the distal end portion, and make cost and image quality of the single use endoscope compatible. Furthermore, most of parts of the endoscope are single-use and the distal end portion is subjected to cleaning and sterilization processing by a vendor, so that it is possible to reduce a cost burden of a user (e.g., hospital) who uses the endoscope. In addition, when the illumination unit such as the LED is included in the distal end portion, the illumination unit is also reused together with the imaging element.

Furthermore, the imaging element and the imaging optical system (objective lens) may be integrally formed in the single use endoscope device, and reused. The most expensive component among components of the distal end portion of the endoscope is the imaging element (the CMOS or the CCD), and the second expensive component is the imaging optical system. Furthermore, although a factor on which image quality of the endoscope depends is a focal point position, generally, a distance between the imaging element and the imaging optical system is adjusted, and an arrangement thereof is fixed such that a range of 3 mm to 100 mm can be observed, and an optimal focal position is approximately 10 mm. Furthermore, an adhesive is used to fix the imaging element and the imaging optical system, and therefore it is difficult to disassemble the imaging element and the imaging optical system during reuse. Due to the above situation, it is wise to "reuse" the imaging element and the imaging optical system as an integrated component. In addition, an element of the illumination optical system (e.g., a white LED) is cheap, and, since arrangement position adjustment accuracy is not strict, single use is valid.

The operation unit, the curved portion, the soft portion, the connector portion and the connector cable portion in the single use endoscope are formed by a resin (the resin which is sufficiently softer than the distal end portion) having higher flexibility than the distal end portion. By using the resin of the high flexibility, it is possible to realize the endoscope of good operability and low cost. Furthermore, at least the curved portion and the soft portion adopt the multi-lumen structure, and different usages are assigned to the respective tube portions. For example, the cable (including the power line and the signal line) can be inserted in the one tube portion, and the other tube portion can be used as an air supply passage, a water supply passage, or a suction passage. Furthermore, the operation unit is provided with a switch which electrically switches ON/OFF of one or more functions of suctioning, air supply, and water supply. The electrical switch operates suctioning, air supply, and water supply, so that it is possible to completely prevent a blowout due to a reverse flow of a mucus or a blood. The soft portion internally includes, for example, a tube which is harder than the resin (the resin which covers an outer side of the endoscope) having the multi-lumen structure. Furthermore, the soft portion may include a metal closely wound coil, and the soft portion may be configured not to be curved in conjunction with curving of the curved portion when the curved portion is curved. Consequently, the soft portion can be configured not to be curved in conjunction with curving of the curved portion when the user (operator) operates the operation unit to curve the curved portion.

The distal end portion includes the power supply terminal and the signal terminal which are formed by a pin contact contact point. Furthermore, at least the imaging element (the LED illumination unit, too, in a case where the LED light unit is included in the distal end portion) receives a supply of power and a signal via the power supply terminal and the signal terminal. By so doing, it is possible to detach the distal end portion from the main body of the single use endoscope.

The distal end portion is not provided with the air supply nozzle and the water supply nozzle, and is provided with the forceps port, the air supply port which is used in place of the air supply nozzle, and the water supply port and the water jet port which are used in place of the water supply nozzle. Consequently, it is possible to suppress the cost for producing the distal end portion, simplify an assembly process of the single use endoscope, and consequently suppress cost of the single use endoscope. For example, the forceps pipe, the air supply tube, the water supply tube and the sub water supply tube are inserted through the operation unit, the soft portion and the curved portion, and protrude from the end surface of the curved portion. Furthermore, the forceps pipe, the air supply tube, the water supply tube, and the sub water supply tube protruding from the end surface of the curved portion are inserted in each of the forceps port, the air supply port, the water supply port, and the water jet port of the distal end portion to couple the distal end portion and the curved portion, and further fix the distal end portion and the curved portion by adhesive means such as an adhesive or a tape.

Furthermore, the memory (e.g., the RFID tag) is provided to the above single use endoscope, and an identification number unique to the single use endoscope is stored therein. By so doing, it is possible to easily manage each single use endoscope. Furthermore, by using this unique identification number, it is possible to trace each state from producing to discarding.

Disclosed matters of the present embodiment are as follows.

(1) Disclosed Matter 1

A single use endoscope device which is inserted in a subject includes:

a distal end portion which includes at least an imaging element;

an operation unit which operates the endoscope device;
a curved portion which can be curved inside the subject by operating the operation unit;
a fractured portion which detaches the distal end portion from the curved portion; and
a soft portion which is extended from the operation unit to the curved portion, wherein
the distal end portion or at least the imaging element included in the distal end portion is reused, and
a portion located closer to a side of the operation unit than a reuse portion is formed as a single use portion.

(2) Disclosed Matter 2

The single use endoscope device according to disclosed matter 1, wherein the distal end portion includes the imaging element and, in addition, an imaging optical system, and the imaging optical system is reused together with the imaging element.

(3) Disclosed Matter 3

The single use endoscope device according to disclosed matter 1 or 2, wherein the curved portion and the soft portion adopt a multi-lumen structure.

(4) Disclosed Matter 4

The single use endoscope device according to disclosed matter 3, wherein
the soft portion internally includes a tube which adopts the multi-lumen structure and is harder than a resin, and
the soft portion is configured not to be curved in conjunction with curving of the curved portion when the curved portion is curved.

(5) Disclosed Matter 5

The single use endoscope device according to any one of disclosed matters 1 to 4, wherein the distal end portion includes a forceps port, an air supply port which is used in place of an air supply nozzle, and a water supply port and a water jet port which are used in place of a water supply nozzle.

(6) Disclosed Matter 6

The single use endoscope device according to disclosed matter 5, wherein a forceps pipe, an air supply tube, a water supply tube, and a sub water supply tube are inserted through the operation unit, the soft portion, and the curved portion, and protrude from an end surface of the curved portion, the forceps pipe, the air supply tube, the water supply tube, and the sub water supply tube protruding from the end surface of the curved portion are inserted in each of the forceps port, the air supply port, the water supply port, and the water jet port of the distal end portion, and the distal end portion and the curved portion are coupled.

(7) Disclosed Matter 7

The single use endoscope device according to any one of disclosed matters 1 to 6, wherein at least part of an insertion portion including the distal end portion, the curved portion, and the soft portion includes a coating layer formed by a hydrophilic coating material.

(8) Disclosed Matter 8

The single use endoscope device according to any one of disclosed matters 1 to 7, wherein the distal end portion includes a single use treatment tool.

(9) Disclosed Matter 9

The single use endoscope device according to disclosed matter 8, wherein the treatment tool is an electric knife which includes an electrode portion, and operates when receiving a supply of a high frequency current.

(10) Disclosed Matter 10

The single use endoscope device according to any one of disclosed matters 1 to 9, wherein an insertion portion including the distal end portion, the curved portion, and the soft portion is integrally molded by a resin.

(11) Disclosed Matter 11

The single use endoscope device according to disclosed matter 10, wherein the distal end portion formed by the resin includes an insulation resin layer, and a resin layer in which a magnetic material is dispersed.

(12) Disclosed Matter 12

The single use endoscope device according to any one of disclosed matters 1 to 11, wherein the fractured portion is formed by a fractured portion of a tube shape which covers a coupling portion of the distal end portion and the curved portion.

(13) Disclosed Matter 13

The single use endoscope device according to disclosed matter 12, wherein
the fractured portion is formed between a distal end of the distal end portion and a predetermined position of the curved portion, and
a diameter of the fractured portion is configured to be smaller than a diameter of a portion other than the fractured portion.

(14) Disclosed Matter 14

The single use endoscope device according to any one of disclosed matters 1 to 13, wherein the operation unit, a connector portion which includes a connector which is connected with a processor of an endoscope system, and a connector cable portion which is extended from the operation unit to the connector portion are included in the single use portion.

REFERENCE SIGNS LIST

1 ENDOSCOPE SYSTEM
10 ENDOSCOPE
20 VIDEO PROCESSOR
101 DISTAL END PORTION
102 CURVED PORTION
103 SOFT PORTION
104 OPERATION UNIT
105 CONNECTOR CABLE PORTION
106 CONNECTOR PORTION

The invention claimed is:

1. A single use endoscope device which is configured to be inserted inside a subject, the single use endoscope device comprising:
a distal end portion which includes at least an imaging element;
an operation unit which is configured to operate the endoscope device;
a curved portion which can be curved inside the subject by operating the operation unit;
a fracture portion configured to fracture when the distal end portion is detached from the curved portion; and
a soft portion which extends from the operation unit to the curved portion,
wherein a reusable portion comprises the distal end portion or at least the imaging element included in the distal end portion, and
wherein a part of the endoscope device that is proximal of the reusable portion is formed as a single use portion,
wherein the fracture portion is at least part of a tube shape which covers a coupling portion of the distal end portion and the curved portion.

2. The single use endoscope device according to claim 1, wherein the distal end portion includes an imaging optical system, and the imaging optical system is reusable together with the imaging element.

3. The single use endoscope device according to claim 1, wherein the curved portion and the soft portion have a multi-lumen structure.

4. The single use endoscope device according to claim 3, wherein
the soft portion internally includes a tube which has the multi-lumen structure and is harder than a resin used for an outer portion of the soft portion, and
the soft portion is configured not to be curved in conjunction with curving of the curved portion when the curved portion is curved.

5. The single use endoscope device according to claim 1, wherein the distal end portion includes a forceps port, an air supply port which is configured to receive a corresponding supply tube from the curved portion, and a water supply port and a water jet port which are each configured to receive a corresponding supply tube from the curved portion.

6. The single use endoscope device according to claim 5, wherein a forceps pipe, an air supply tube, a water supply tube, and a sub water supply tube are inserted through the operation unit, the soft portion, and the curved portion, and protrude from an end surface of the curved portion, the forceps pipe, the air supply tube, the water supply tube, and the sub water supply tube protruding from the end surface of the curved portion are inserted in each of the forceps port, the air supply port, the water supply port, and the water jet port of the distal end portion, and the distal end portion and the curved portion are coupled.

7. The single use endoscope device according to claim 1, wherein at least part of an insertion portion including the distal end portion, the curved portion, and the soft portion includes a coating layer formed by a hydrophilic coating material.

8. The single use endoscope device according to claim 1, wherein the distal end portion includes a single use treatment tool.

9. The single use endoscope device according to claim 8, wherein the treatment tool is an electric knife which includes an electrode portion, and operates when receiving a supply of a high frequency current.

10. The single use endoscope device according to claim 1, wherein an insertion portion including the distal end portion, the curved portion, and the soft portion is integrally molded by a resin.

11. The single use endoscope device according to claim 10, wherein the distal end portion formed by the resin includes an insulation resin layer, and a resin layer in which a magnetic material is dispersed.

12. The single use endoscope device according to claim 1, wherein
the fracture portion is formed between a distal end of the distal end portion and a predetermined position of the curved portion, and
a diameter of the fracture portion is configured to be smaller than a diameter of a portion other than the fracture portion.

13. The single use endoscope device according to claim 1, wherein the operation unit, a connector portion which includes a connector which is connected with a processor of an endoscope system, and a connector cable portion which is extended from the operation unit to the connector portion are included in the single use portion.

14. A single use endoscope device which is configured to be inserted inside a subject, the single use endoscope device comprising:
a distal end portion which includes at least an imaging element;
an operation unit which is configured to operate the endoscope device;
a curved portion which can be curved inside the subject by operating the operation unit;
a fracture portion which is configured to fracture when the distal end portion is detached from the curved portion; and
a soft portion which extends from the operation unit to the curved portion,
wherein the distal end portion or at least the imaging element included in the distal end portion is reusable, and
wherein a portion of the endoscope device located closer to a side of the operation unit than a reusable portion of the endoscope device is formed as a single use portion, and
wherein the fracture portion is at least part of a tube shape which covers a coupling portion of the distal end portion and the curved portion.

15. The single use endoscope device according to claim 14, wherein the fracture portion is configured to fracture without damage to the imaging element when the distal end portion is detached from the curved portion.

16. The single use endoscope device according to claim 15, wherein the distal end portion includes the imaging element and an imaging optical system, and
wherein the imaging optical system is reusable together with the imaging element.

17. The single use endoscope device according to claim 15, wherein the curved portion and the soft portion have a multi-lumen structure.

18. The single use endoscope device according to claim 17, wherein the soft portion internally includes a tube which has the multi-lumen structure and is harder than a resin used for an outer portion of the soft portion, and
wherein the soft portion is configured not to be curved in conjunction with curving of the curved portion when the curved portion is curved.

19. The single use endoscope device according to claim 15, wherein at least part of an insertion portion including the distal end portion, the curved portion, and the soft portion includes a coating layer formed by a hydrophilic coating material.

20. The single use endoscope device according to claim 15, wherein the fracture portion is formed between a distal end of the distal end portion and a predetermined position of the curved portion, and
wherein an outer diameter of the fracture portion is configured to be smaller than an outer diameter of the distal end portion, and
wherein the outer diameter of the fracture portion is configured to be smaller than an outer diameter of the curved portion.

* * * * *